(12) United States Patent
Hensler et al.

(10) Patent No.: US 11,617,836 B2
(45) Date of Patent: Apr. 4, 2023

(54) BONE DELIVERY APPARATUS AND METHODS

(71) Applicant: H & M INNOVATIONS, LLC, Wilmington, NC (US)

(72) Inventors: Robert Sean Hensler, Wilmington, NC (US); Thomas Eric Melin, Wilmington, NC (US); Ryan Shane Gorman, Charlotte, NC (US); Thomas James Philpott, Charlotte, NC (US); Michael Starkey, Kent, OH (US); Lauren Mazzio, Concord, NC (US)

(73) Assignee: H & M INNOVATIONS, LLC, Wilmington, NC (US)

( * ) Notice: Subject to any disclaimer, the term of this patent is extended or adjusted under 35 U.S.C. 154(b) by 703 days.

(21) Appl. No.: 16/538,810

(22) Filed: Aug. 12, 2019

(65) Prior Publication Data

US 2019/0358406 A1    Nov. 28, 2019

Related U.S. Application Data

(63) Continuation of application No. 14/955,014, filed on Nov. 30, 2015, now Pat. No. 10,376,648, which is a continuation of application No. 14/824,073, filed on Aug. 11, 2015, now abandoned.

(60) Provisional application No. 62/036,111, filed on Aug. 11, 2014, provisional application No. 62/036,110, filed on Aug. 11, 2014.

(51) Int. Cl.
*A61M 5/315*    (2006.01)

(52) U.S. Cl.
CPC ..... *A61M 5/31511* (2013.01); *A61M 2202/06* (2013.01)

(58) Field of Classification Search
CPC ............ A61M 5/31511; A61M 5/3129; A61M 5/3134; A61M 2202/06; A61M 2005/3142; A61B 17/88; A61F 2/4601; A61F 2002/4623; A61F 2002/4625; A61F 2002/4627

See application file for complete search history.

(56) References Cited

U.S. PATENT DOCUMENTS

2004/0127987 A1 *  7/2004  Evans ..................... A61P 19/02
                                                     623/23.73
2008/0009823 A1 *  1/2008  McKay ............. A61B 17/7044
                                                     604/218

\* cited by examiner

*Primary Examiner* — Laura A Bouchelle
*Assistant Examiner* — John A Doubrava
(74) *Attorney, Agent, or Firm* — Tillman Wright, PLLC; Chad D. Tillman

(57) ABSTRACT

Apparatus for delivery of bone includes a syringe body and a plunger. The syringe body includes a tip at a bottom thereof, a funnel-shaped top at the top thereof, and a tubular section having a generally cylindrical interior wall defining a passageway extending from the funnel-shaped top to the tip. The plunger includes an elongate piston, a press head, and a handle. The piston extends between the press head at a lower end of the plunger, and the handle at an upper end of the plunger. The plunger is removably received within the passageway, with an extent of the plunger extending out of the funnel-shaped top away from the syringe body. The syringe body may be loaded with one or more bone pellets or cartridges containing bone.

8 Claims, 40 Drawing Sheets

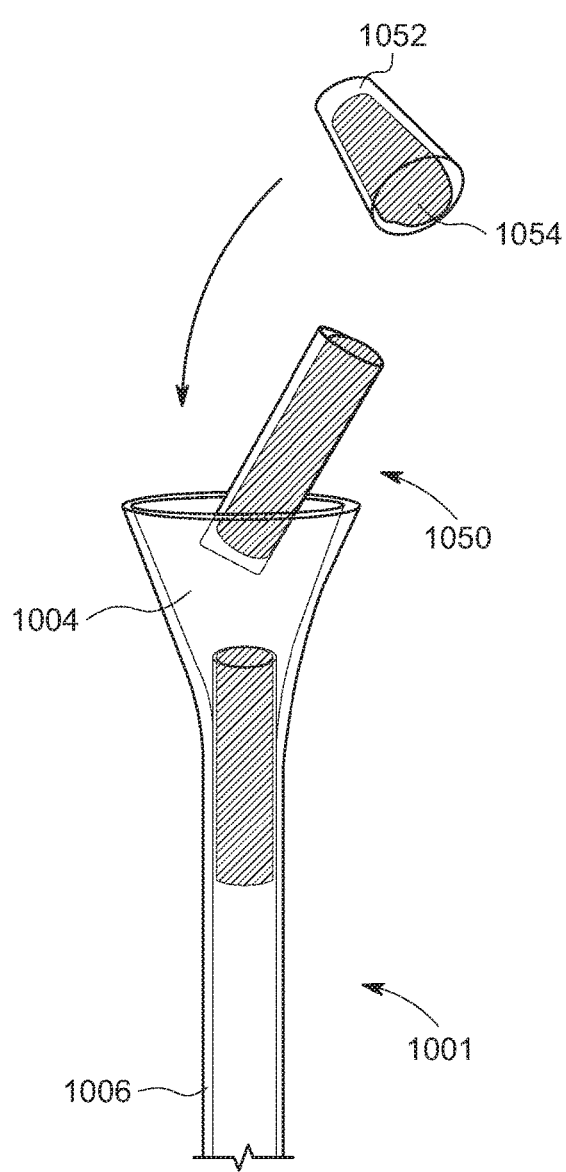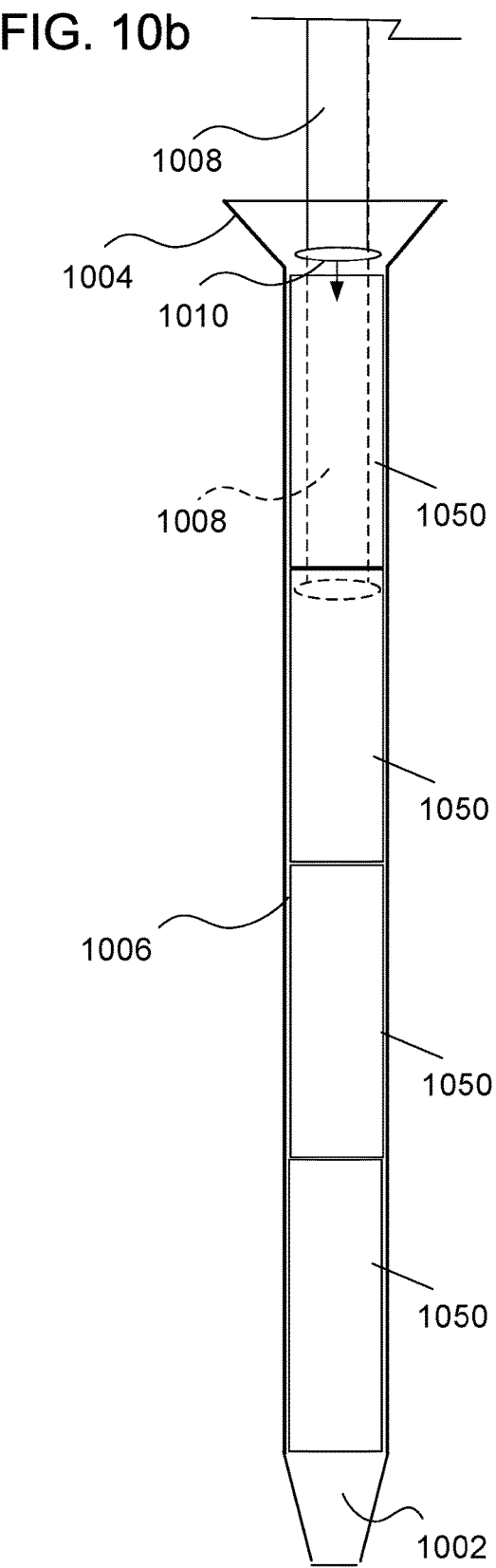
FIG. 10a
FIG. 10b

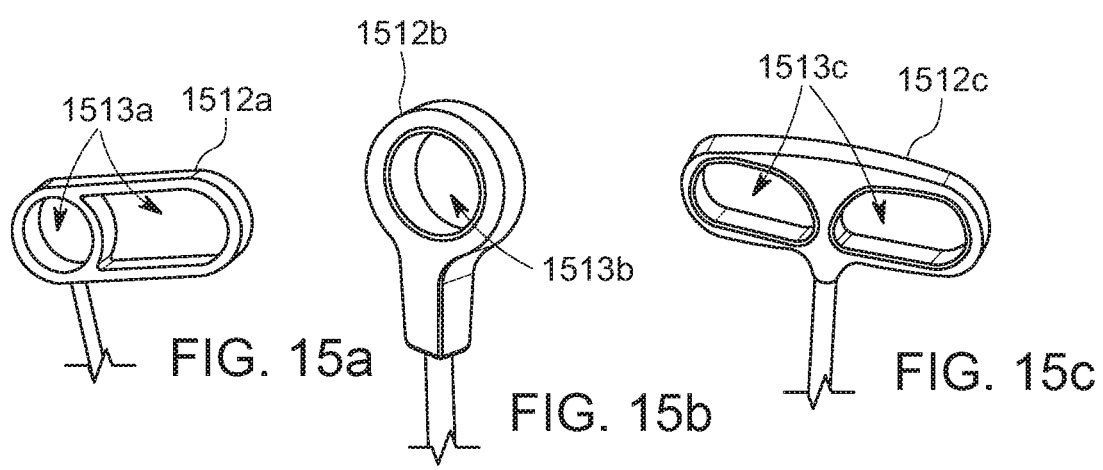

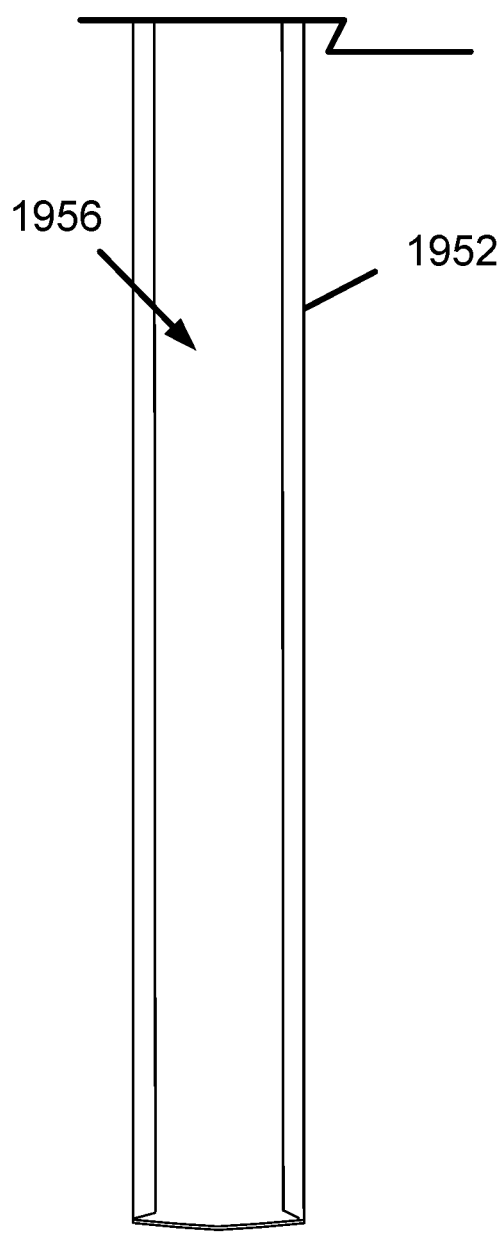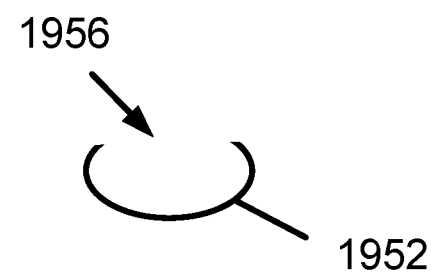
FIG. 20a
FIG. 20b

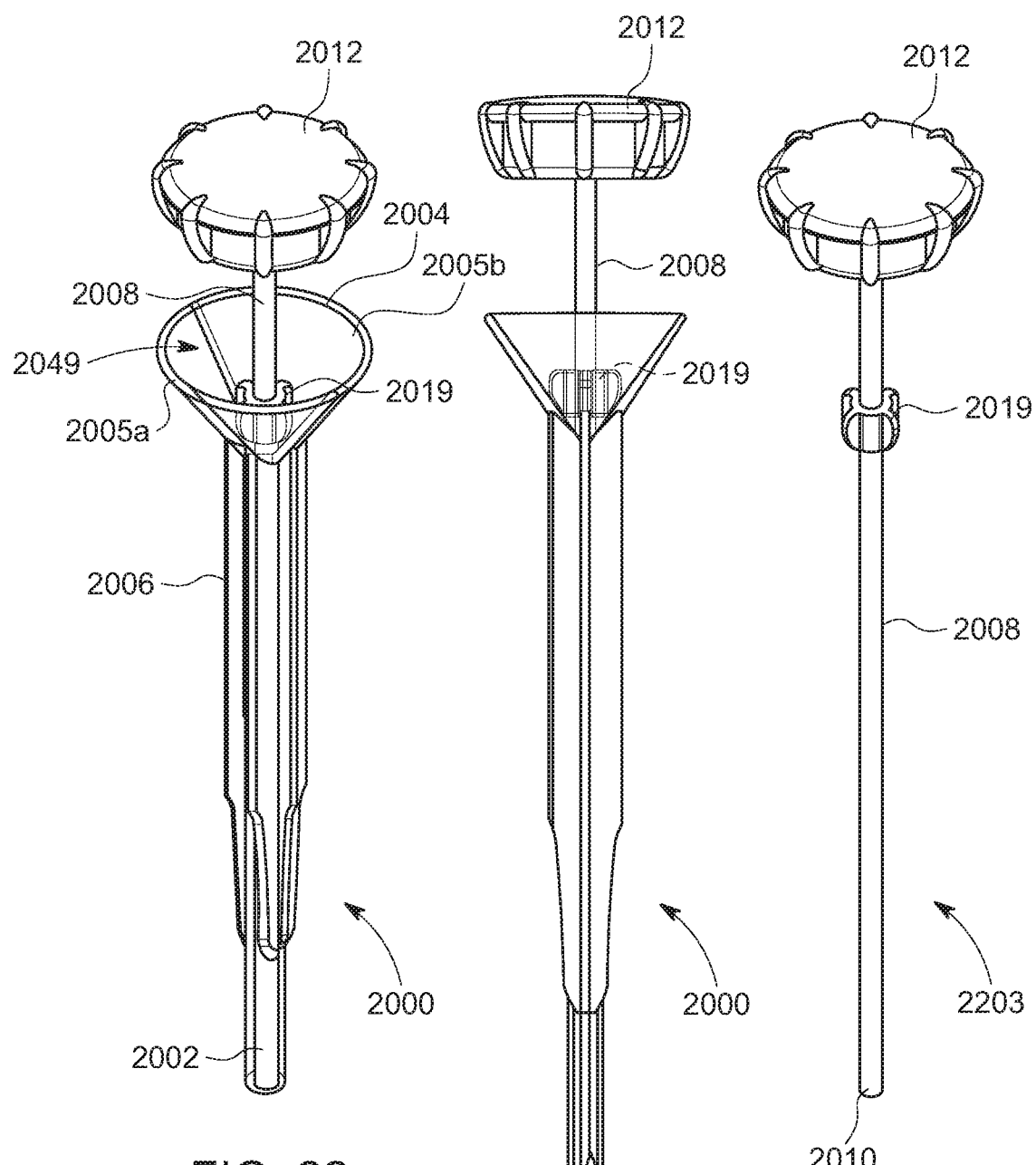

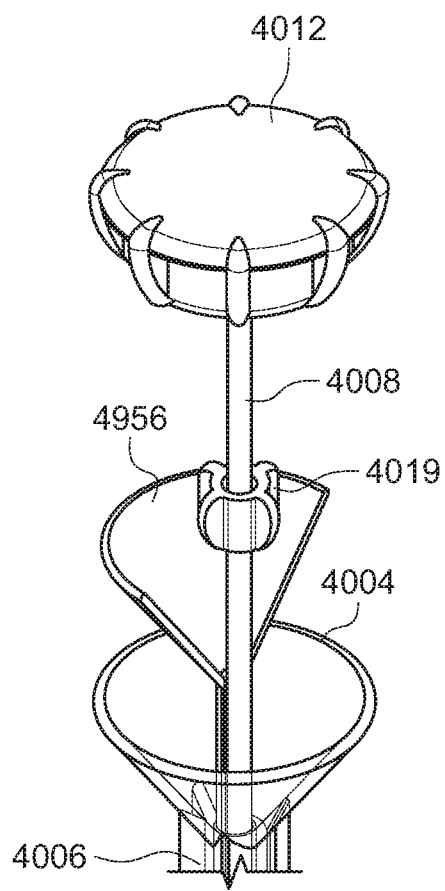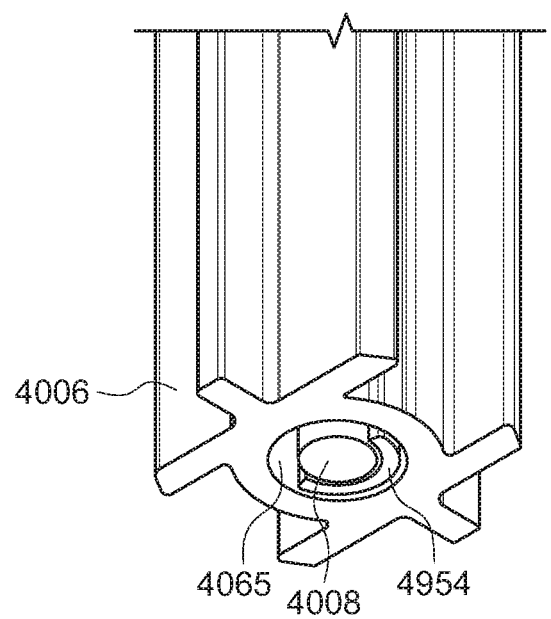
FIG. 26a
FIG. 26b

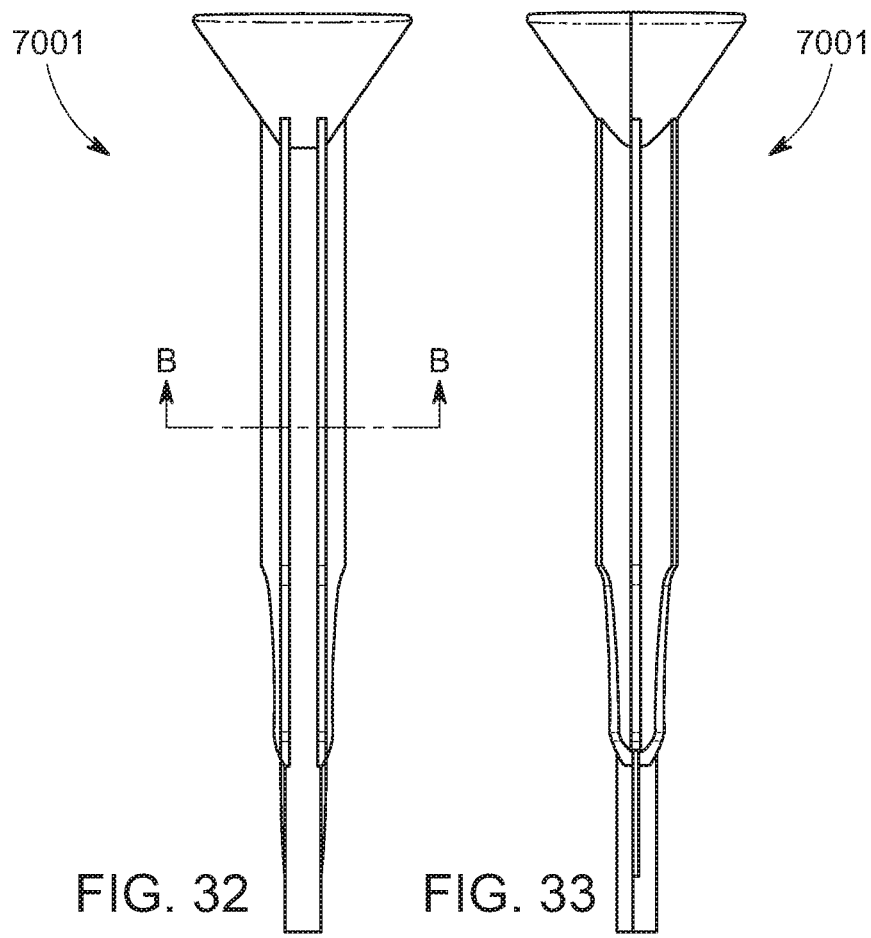
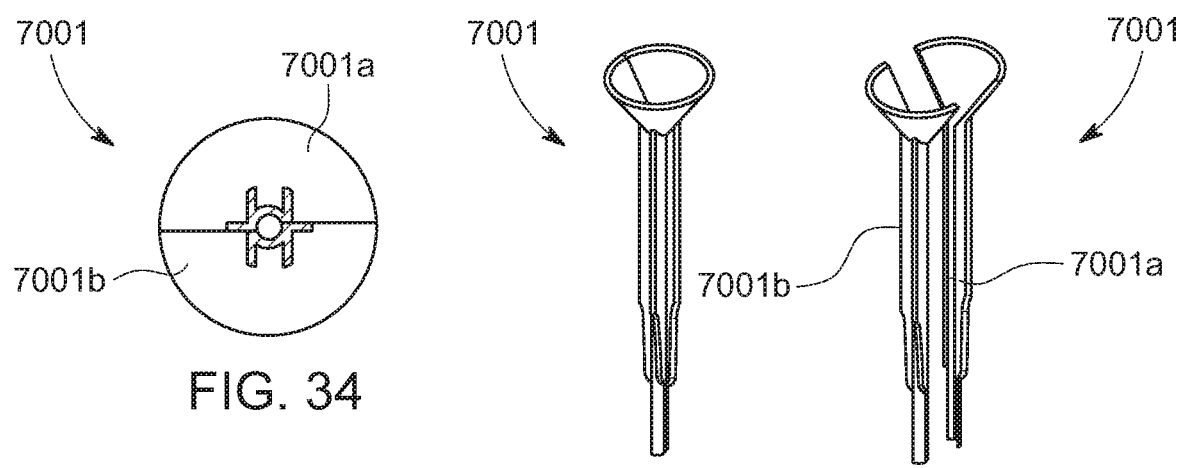

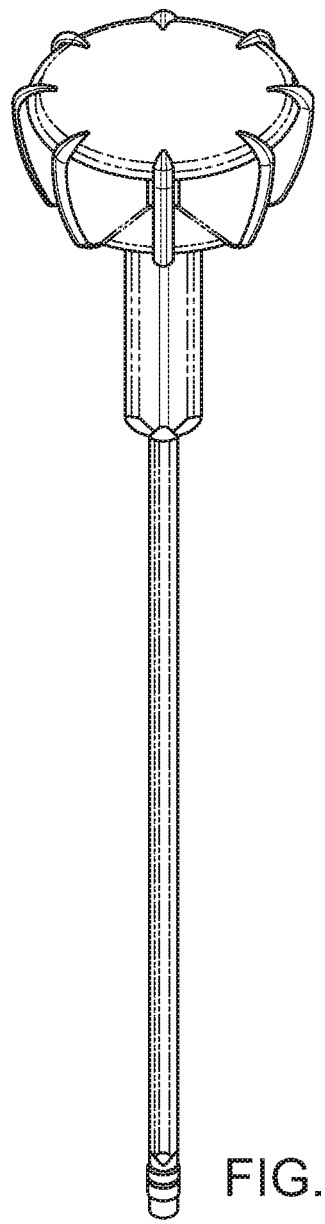
FIG. 37
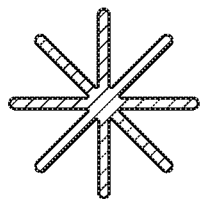
FIG. 39
FIG. 40
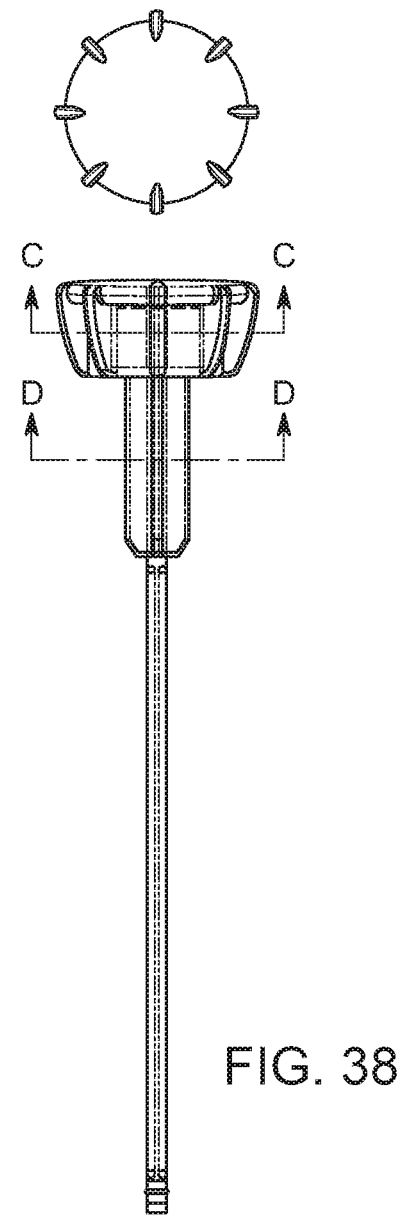
FIG. 38
FIG. 42 — OVERMOLDED WIPER
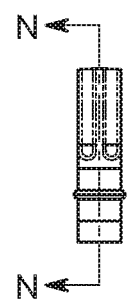
FIG. 41

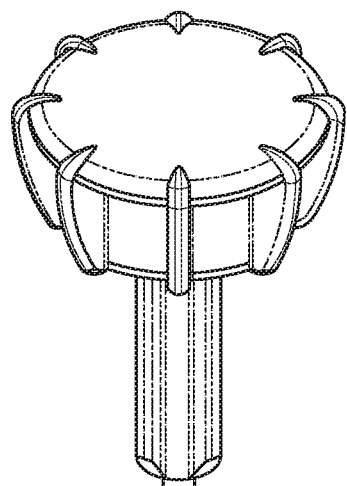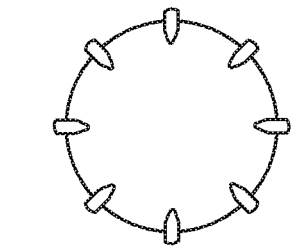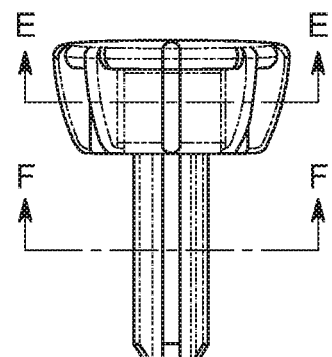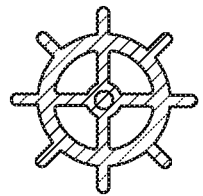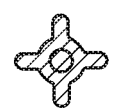
FIG. 44
FIG. 46
FIG. 47
FIG. 45

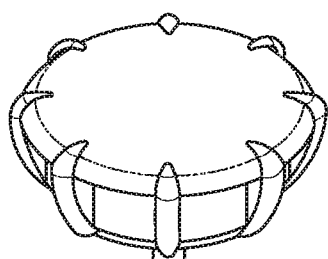
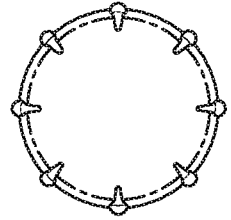
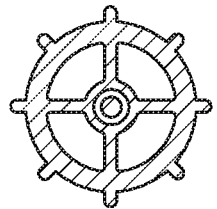
FIG. 54
FIG. 55
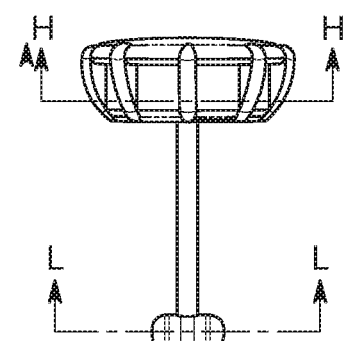
FIG. 52
FIG. 53

BONE DELIVERY APPARATUS AND METHODS

CROSS-REFERENCE TO RELATED APPLICATION

The present application is a U.S. continuation patent application of, and claims priority under 35 U.S.C. § 120 to, U.S. nonprovisional patent application Ser. No. 14/955,014, filed Nov. 30, 2015, now U.S. Pat. No. 10,376,648, which '014 application is a U.S. continuation patent application of, and claims priority under § 120 to, U.S. nonprovisional patent application Ser. No. 14/824,073, filed Aug. 11, 2015, which '073 application is incorporated by reference herein, and which '073 application is a U.S. nonprovisional patent application of, and claims priority under 35 U.S.C. § 119(e) to each of: U.S. provisional patent application 62/036,110, filed Aug. 11, 2014, which '110 application is incorporated by reference herein; and U.S. provisional patent application 62/036,111, filed Aug. 11, 2014, which '111 application is incorporated by reference herein. Additionally, the drawings and appendix of the '111 application are in the Appendix, which is incorporated by reference herein.

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE INVENTION

The present invention generally relates to the delivery of bone and, in particular, to the delivery of autologous bone to a patient during surgery or other medical procedure.

SUMMARY OF THE INVENTION

The present invention includes many aspects and features. Moreover, while many aspects and features relate to, and are described in, the context of the delivery of autologous bone, the present invention is not limited to such use only, as will become apparent from the following summaries and detailed descriptions of aspects, features, and one or more embodiments of the present invention. Indeed, bone from other sources than the patient—as well as other organic tissue and matter—can be delivered to a body using the apparatus, systems, and methods described herein.

Accordingly, in one aspect of the present invention, an apparatus for delivery of bone comprises a syringe body and a plunger. The syringe body comprises a tip at a bottom thereof; a funnel-shaped top at the top thereof; and a tubular section having a generally cylindrical interior wall defining a passageway extending from the funnel-shaped top to the tip. The plunger comprises an elongate piston, a press head, and a handle. The piston extends between the press head at a lower end of the plunger and the handle at an upper end of the plunger. The plunger is removably received within the passageway, with an extent of the plunger extending out of the funnel-shaped top away from the syringe body.

In a feature of this aspect, the piston is dimensioned to be received through the funnel-shaped top into—and extend within—the passageway of the tubular section of the cylindrical body of the syringe.

In a feature of this aspect, the lower press head of the piston preferably slides in sealing abutment with the surface of the passageway of the tubular section so as to push any matter contained within the passageway toward the tip when a force is applied to the handle pushing the piston to a further extent within the passageway, whereby matter contained within the passageway thereby is expelled through a distal opening in the tip. The sealing engagement may be located at the press head or spaced at a distance to the press head; in a preferred embodiment, a sealing ring is located at a distance to the press head, extends around the piston, and engages the interior of the passageway in sealing engagement between the piston and the interior of the passageway.

In a feature, the tubular section comprises threads by which the tip is removably attachable in threaded engagement by screwing the tip onto a lower threaded end portion of the body of the syringe. Preferably a plurality of tips are provided having different internal diameters as may be desired, including a tip having a 4 mm diameter and a tip having a 2 mm diameter for delivery of bone. Furthermore, the threads preferably are on the outside of the end portion of the tubular section, with a corresponding mating structure on the inside of each interchangeable tip. All of this is shown, for example, by consideration of FIGS. 60-65.

In another feature, the funnel-shaped top and the tubular section consist of a single molded piece to which the tip is removably attachable in threaded engagement by screwing the tip onto a lower threaded end portion of the body of the syringe. The single molded piece may be transparent. Alternatively, the funnel-shaped top and the tubular section comprise two pieces that are welded together to form a single, integral piece.

In a feature of this aspect, the tip is transparent.

In a feature of this aspect, the tip is opaque.

In a feature of this aspect, the body—including the tip—consists of a single molded piece.

In a feature of this aspect, the piston consists of a single molded piece.

In a feature of this aspect, the apparatus further comprises a plurality of ribs in the form of wings, each longitudinally extending along the funnel-shaped top and an upper portion of the tubular section of the syringe. At least the funnel-shaped top, the tubular section, and the plurality of ribs preferably consist collectively of a single molded piece.

In a feature of this aspect, the tip is removably attachable in threaded engagement to the tubular section, and further comprising a second tip that is interchangeable with the first tip and is removably attachable in threaded engagement to the tubular section. Each of the tips preferably includes a different profile for different flow delivery of material when the apparatus is used.

In a feature of this aspect, the tip is flexible and elastic, the tip self-returning to an initial position after deflection or bending.

In a feature of this aspect, the tip is flexible but not elastic and thus remains in a deflected or bent position without self-returning.

In a feature of this aspect, the apparatus further comprises a ribbed structure formed in the handle and in the piston. Furthermore, the apparatus preferably includes one or more thermoplastic elastomers molded between or over the ribbed structure of the handle.

In a feature of this aspect, the handle is generally offset in a radial direction from a longitudinal axis of the piston.

In a feature of this aspect, the apparatus further comprises ribs formed in the piston along an extent of the piston between the handle and an annular flange section. The annular flange section preferably mates with an interior circumferential perimeter of the funnel-shaped top of the syringe body. Furthermore, ribs preferably extend from the annular flange section in a longitudinal direction away from the handle extend at an angle matching an angle of an inside funnel-shaped surface of the funnel-shaped top of the syringe body for an abutting fit therewith, whereby the annular flange section and surfaces defined by upper edges of the ribs define a physical stop against extension of the plunger within the passageway of the syringe body.

In a feature of this aspect, the handle defines one or more openings each for receiving one or more digits of a hand when the handle is grasped. Preferably, the one or more openings are entirely enclosed by the handle.

In a feature of this aspect, the handle is symmetrical with respect to a longitudinal axis of the piston.

In a feature of this aspect, the handle is offset relative to a longitudinal axis of the piston.

In a feature of this aspect, the handle includes a top flat surface for accommodating use of a mallet, if needed, when pushing bone through and out of the passageway of the syringe body.

In a feature of this aspect, the handle is articulated.

In a feature of this aspect, the handle includes a pin about which a top portion of the handle is connected to a bottom portion of the handle and pivots relative thereto, whereby the handle is transitionable between a use configuration and a folded configuration.

In a feature of this aspect, the handle is knobbed shaped and includes ribs extending along the circumferential sides thereof generally in a direction parallel to a longitudinal axis of the piston.

In a feature of this aspect, the handle is integrally formed with the piston. For example, the handle and piston may consist of a single, molded piece.

In a feature of this aspect, the handle is not integrally formed with the piston.

In a feature of this aspect, the handle is removably attached to an end of the piston. The attachment may be a threaded engagement. The attachment may be a friction fit; the handle may snap onto an end of the piston; the handle may be bonded to the piston; the handle may be overmolded on the piston; and the handle may be adhered to the piston.

In another aspect, a method of delivery of bone comprises using an apparatus in accordance with one of the foregoing aspects.

In a feature of this aspect, the passageway of the tubular section of the syringe body is at least partially filled with the bone by inserting the bone through the funnel-shaped top, the plunger then is inserted through the funnel-shaped top to extend within the passageway of the tubular section; the plunger is further inserted such that the press head at the lower end of the piston engages and pushes the bone toward the tip; placing the tip at the desired location relative to the patient; and further inserting the plunger such that bone is expelled through the opening in the tip. Preferably, the method is used during a medical procedure, and the bone comprises autologous bone, i.e., the patient's bone that is harvested during the procedure.

In another aspect, an apparatus for delivery of bone comprises a syringe body, the syringe body comprising a tip at a bottom thereof, a funnel-shaped top at the top thereof, and a tubular section having a generally cylindrical interior wall defining a passageway extending from the funnel-shaped top to the tip; and a plunger, the plunger comprising an elongate piston, a press head, and a handle. The piston extends between the press head at a lower end of the plunger and the handle at an upper end of the plunger. The plunger is removably received within the passageway, with an extent of the plunger extending out of the funnel-shaped top away from the syringe body. The syringe further comprises a transparent window extending within an opening defined in the tubular section, whereby bone that is contained within the passageway is viewable through the window.

In a feature of this aspect, the window extends along a length of the tubular section between the funnel-shaped top and the tip. The window may extend along the entire length of the tubular section; the window may extend along a length of a lower half of the tubular section and not a lower half of the tubular section; or the window may extend along a length of an upper half of the tubular section and not an upper half of the tubular section. Graduations preferably are provided along the extent of the tubular section adjacent to the window, by which bone contained within the interior space may be measured for delivery. The graduations preferably are equally spaced in linear sequence along the window and are oriented in generally parallel relation to each other. The graduations may be formed in the tubular section; the graduations may comprise indentions in the tubular section; the graduations comprise raised areas in the tubular section; and the graduations may be defined by coloring or other markings made on the surface of the tubular section.

In another aspect, an apparatus for delivery of bone comprises a syringe body and a plunger. The syringe body comprises a tip at a bottom thereof, a funnel-shaped top at the top thereof, and a tubular section having a generally cylindrical interior wall defining a passageway extending from the funnel-shaped top to the tip. The plunger comprises an elongate piston, a press head, and a handle. The piston extends between the press head at a lower end of the plunger, and the handle at an upper end of the plunger. The plunger is removably received within the passageway, with an extent of the plunger extending out of the funnel-shaped top away from the syringe body.

In a feature of this aspect, the piston includes numerical measurement indicators. Moreover, the numerical measurement indicators may be separated by equally spaced, parallel line delineators; and the syringe further may comprise a transparent window extending within an opening defined in the tubular section. The window may be located proximate the funnel-shaped top; and the window may be dimensioned to show there through one-at-a-time a single numerical measurement indicator on the piston. The tubular section also may comprise alignment indicators, wherein a delineator on the piston is aligned with an alignment indicator when a corresponding numerical measurement indicator is seen through the window.

The indicators may be formed in the piston; the indicators may comprise indentions in the piston; the indicators may comprise raised areas of the piston; and the indicators may be defined by coloring or other markings made on the surface of the piston. The delineators may be formed in the piston; the delineators may comprise indentions in the piston; the delineators may comprise raised areas of the piston; and the delineators may be defined by coloring or other markings made on the surface of the piston.

The alignment indicators may comprise indentions in the tubular section; the alignment indicators may comprise raised areas of the tubular section; and the alignment indicators may be defined by coloring or other markings made on the surface of the tubular section.

The window may comprise alignment indicators wherein the alignment indicators may comprise indentions in the window; the alignment indicators comprise raised areas of the window; and the alignment indicators are defined by coloring or other markings made on the surface of the window.

In another aspect, a method of delivery of bone comprises using the apparatus of the aforementioned aspect, including taking readings, each reading taken being of a numerical measurement indicator as seen through the transparent window when the corresponding delineator aligns with the alignment indicators.

In another aspect, an apparatus for delivery of bone comprises a syringe body and a plunger. The syringe body comprises a tip at a bottom thereof, a funnel-shaped top at the top thereof, and a tubular section having a generally cylindrical interior wall defining a passageway extending from the funnel-shaped top to the tip. The plunger comprises an elongate piston, a press head, and a handle. The piston extends between the press head at a lower end of the plunger and the handle at an upper end of the plunger. Furthermore, the piston includes numerical measurement indicators and equally spaced, parallel line delineators corresponding to the numerical measurement indicators. Moreover, the funnel-shaped top is transparent, enabling the indicators and delineators to be seen and read relative to a juncture between the funnel-shaped top and the tubular section In a feature of this aspect, the indicators are formed in the piston. The indicators may comprise indentions in the piston; the indicators comprise raised areas of the piston; and the indicators are defined by coloring or other markings made on the surface of the piston.

In a feature of this aspect, the delineators are formed in the piston. The delineators may comprise indentions in the piston; the delineators may comprise raised areas of the piston; and the delineators are defined by coloring or other markings made on the surface of the piston.

In another aspect, a method of delivering bone comprises using the aforementioned apparatus, including taking readings, each reading taken being of a numerical measurement indicator and/or line delineator as seen through the transparent top when the corresponding delineator aligns with the juncture between the top and the tubular section.

In another aspect, a method relates to loading an apparatus for delivery of bone to a patient during a surgical operation. The apparatus comprises a body including a funnel-shaped top, a lower tip, and a tubular section with a generally cylindrical interior wall defining a passageway extending therebetween. Within this preferred context, the method comprises loading the passageway with bone for delivery by sequentially inserting a plurality of cartridges into the passageway such that the cartridges are stacked in generally axial alignment—one on top of the other—within the passageway of the tubular section, wherein each cartridge comprises a tube having open ends with bone packed therein.

In a feature of this aspect, the tube of each cartridge is generally cylindrical and includes an outer diameter generally corresponding to the inner diameter of the passageway of the tubular section so that a close fit is achieved between the tube and the generally cylindrical interior wall of the passageway of the tubular section. The inner diameter of the tube of each cartridge preferably corresponds generally to the outer diameter of the passageway.

In a feature of this aspect, the apparatus is one of the group of the foregoing described apparatus.

In another aspect, a method for loading an apparatus for delivery of bone to a patient during a surgical operation, the apparatus comprising a body including a funnel-shaped top, a lower tip, and a tubular section with a generally cylindrical interior wall defining a passageway extending therebetween, the method comprising loading the passageway with bone for delivery by sequentially inserting a plurality of bone pellets into the passageway such that the pellets are stacked in generally axial alignment—one on top of the other—within the passageway of the tubular section, wherein each pellet has a generally cylindrical shape.

In a feature of this aspect, the outer diameter of each pellet generally corresponds to the inner diameter of the passageway of the tubular section.

In a feature, the method further comprises the preliminary step of pressing bone into the shape of the bone pellets, preferably by using a clamshell molding press.

In another aspect, a method for loading an apparatus for delivery of bone to a patient during a surgical operation, the apparatus comprising a body including a funnel-shaped top, a lower tip, and a tubular section with a generally cylindrical interior wall defining a passageway extending therebetween, the method comprising inserting a single cartridge into the passageway, wherein the cartridge comprises a tube having open ends and having a curved cross-section generally matching that of the generally cylindrical interior wall of the passageway of the tubular section, and wherein the tube is prefilled with an amount of bone such that the bone does not extend beyond the juncture of the tubular section and the funnel-shaped top when the tube is fully received within the passageway.

In a feature of this aspect, the outer diameter of the tube generally corresponds to the inner diameter of the generally cylindrical interior wall of the passageway, with the tube being slightly smaller such that the tube is be received in close fit with the generally cylindrical interior wall of the passageway, the single tube thereby lining the generally cylindrical interior wall of the passageway.

In a feature of this aspect, the tube is made of a metal or metal alloy.

In a feature of this aspect, a length of the tube at least equals the length of the tubular section such that the tube is received within the entire length of the passageway defined by the tubular section.

In a feature of this aspect, a length of the tube exceeds the length of the tubular section such that the tube is received within the entire length of the passageway defined by the tubular section.

In a feature of this aspect, the tube presents an end extent for gripping by hand for insertion into and removal from the passageway.

The method may further comprises using a plunger having an outer diameter generally corresponding to the inner diameter of the tube to push bone from the tube out of the tip of the apparatus.

The method also further may comprise interchanging an emptied tube with another prefilled tube during the surgical procedure, and loading/reloading and staging a plurality of interchangeable tubes for insertion in the passageway during the surgical operation.

In a feature of this aspect, a longitudinal opening extends the length of the tube.

In a feature of this aspect, the tube is entirely enclosed circumferentially with no longitudinal opening.

In another aspect, a kit for bone delivery comprises a syringe and a plurality of cartridges for use in the syringe.

In another aspect, a kit comprises an aforementioned apparatus.

Another aspect comprises a method of using an aforementioned apparatus.

Additional aspects and features are disclosed below and in the drawings.

Furthermore, in addition to the aforementioned aspects and features of the present invention, it should be noted that the present invention further encompasses the various possible combinations and subcombinations of such aspects and features. Thus, for example, any aspect may be combined with an aforementioned feature in accordance with the present invention without requiring any other aspect or feature.

BRIEF DESCRIPTION OF THE DRAWINGS

One or more preferred embodiments of the present invention now will be described in detail with reference to the accompanying drawings.

FIG. 7b is a perspective view of three additional tips that are interchangeable, each of which is configured to be screwed onto the body of the syringe of FIG. 7a.

FIG. 10a illustrates a preferred embodiment of a method for loading a syringe for delivery of bone in accordance with one or more aspects and features of the invention.

FIG. 10b also illustrates a preferred embodiment of a method for loading a syringe for delivery of bone in accordance with one or more aspects and features of the invention.

FIGS. 13a, 13b, 14, 15a, 15b, 15c, 16a, 16b, 16c, 16d, 16e, 16f, 16g, 16h, 17a, 17b, 17c, 18a and 18b each is a perspective view of one of various alternative handles in accordance with one or more aspects and features of the invention.

FIG. 20a is a schematic top plan view of a cartridge similar to the cartridge of FIG. 19.

FIG. 20b is a schematic cross-sectional view of the cartridge of FIG. 20a.

FIG. 21a is a perspective view of an apparatus for delivery of bone in accordance with yet another embodiment of the present invention.

FIG. 21b is a perspective view of a plunger of the apparatus of FIG. 21a.

FIG. 22a is a perspective view of another apparatus for delivery of bone in accordance with yet another embodiment of the present invention.

FIG. 22b is an elevational view of the apparatus of FIG. 22a for delivery of bone.

FIG. 22c is a perspective view of a plunger of the apparatus of FIG. 22a.

FIG. 23a is a perspective view of an apparatus for delivery of bone in accordance with yet another embodiment of the present invention.

FIG. 23b is a perspective view of a plunger of the apparatus of FIG. 23a.

FIG. 24a is a perspective view of an apparatus for delivery of bone in accordance with yet another embodiment of the present invention.

FIG. 24b is another perspective view of the apparatus of FIG. 24a.

FIG. 25a is a perspective view of the cartridge of the apparatus of FIG. 24a.

FIG. 25b is a perspective view of the cartridge of the plunger of FIG. 24a.

FIG. 26a is another view, similar to that of FIG. 24b, but focusing on an upper portion of the apparatus of FIG. 24a.

FIG. 26b is a cross-sectional view of the apparatus of FIG. 24a taken along the line A-A.

FIG. 27c is a cross-sectional view of the upper portion of the apparatus of FIG. 27a.

FIG. 32 is a side view of a body of a syringe used in an apparatus for delivery of bone in accordance with yet another embodiment of the present invention, wherein the syringe body is formed by welding two body portions together.

FIG. 33 is an additional side view of the syringe body of FIG. 32.

FIG. 34 is a cross-sectional view along the line B-B of FIG. 32.

FIG. 35 is a perspective view of the syringe body of FIG. 32.

FIG. 36 is an exploded perspective view of the syringe body of FIG. 32.

FIG. 37 is a perspective view of a plunger used in an apparatus for delivery of bone in accordance with yet another embodiment of the present invention.

FIG. 38 is a side view of the plunger of FIG. 37.

FIG. 39 is a cross-sectional view of the plunger of FIG. 38 taken along the line C-C.

FIG. 40 is a cross-sectional view of the plunger of FIG. 38 taken along the line D-D.

FIG. 41 is a view of the distal end of the plunger of FIG. 38.

FIG. 42 is a cross-sectional view of the distal end of FIG. 41 taken along the line N-N; it will be appreciated that as seen in FIGS. 41 and 42, the distal end of the plunger includes an overmolded wiper.

FIG. 44 is a perspective view of a plunger used in an apparatus for delivery of bone in accordance with yet another embodiment of the present invention.

FIG. 45 is a side view of the plunger of FIG. 44.

FIG. 46 is a cross-sectional view of the plunger of FIG. 45 taken along the line E-E.

FIG. 47 is a cross-sectional view of the plunger of FIG. 45 taken along the line F-F.

FIG. 52 is a perspective view of a plunger used in an apparatus for delivery of bone in accordance with yet another embodiment of the present invention.

FIG. 53 is a side view of the plunger of FIG. 52.

FIG. 54 is a cross-sectional view of the plunger of FIG. 53 taken along the line H-H.

FIG. 55 is a cross-sectional view of the plunger of FIG. 53 taken along the line L-L.

DETAILED DESCRIPTION

Figure 1:
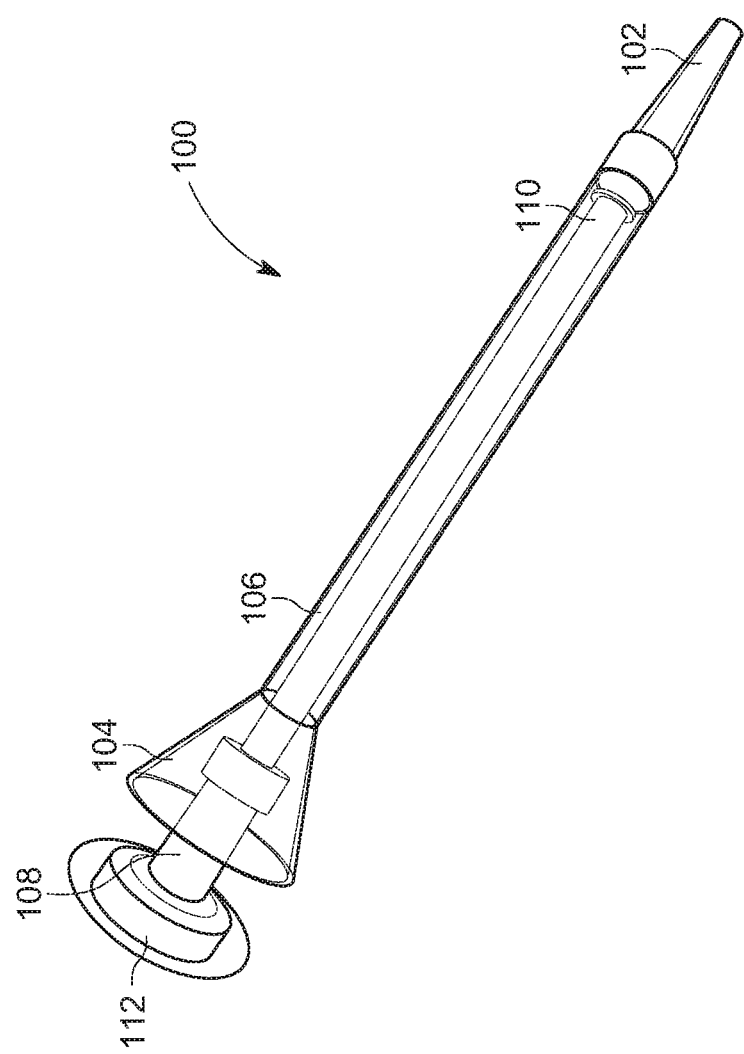
FIG. 1 is a perspective view of an apparatus for delivery of bone in accordance with a first embodiment of the present invention, wherein the apparatus comprises a syringe 100.

As a preliminary matter, it will readily be understood by one having ordinary skill in the relevant art ("Ordinary Artisan") that the present invention has broad utility and application. As should be understood, any embodiment may incorporate only one or a plurality of the above-disclosed aspects of the invention and may further incorporate only one or a plurality of the above-disclosed features. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. As should be understood, any embodiment may incorporate only one or a plurality of the above-disclosed aspects of the invention and may further incorporate only one or a plurality of the above-disclosed features. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention in any claim of a patent issuing here from, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the issued claim(s) rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Regarding applicability of 35 U.S.C. § 112(f), no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Additionally, as used herein, "bone" means material comprising bone chips, bone tissue, and combinations thereof.

Referring now to the drawings, one or more preferred embodiments of the present invention are next described. The following description of one or more preferred embodiments is merely exemplary in nature and is in no way intended to limit the invention, its implementations, or uses.

A First Embodiment

Accordingly, a perspective view of an apparatus for delivery of bone in accordance with a first embodiment of the present invention is shown in FIG. 1 and comprises a syringe 100. The syringe 100 comprises a tip 102 at a bottom thereof, a funnel-shaped top 104, and a tubular section 106 with a generally cylindrical interior wall defining a passageway extending from the funnel-shaped top to the tip 102. The syringe 100 further comprises a plunger comprising an elongate piston 108. The plunger further comprises a press head 110 and a handle 112, with the piston 108 extending between the press head 110 at a lower end thereof and the handle 112 at an upper end thereof.

The piston 108 is dimensioned to be received through the funnel-shaped top 104 into—and extend within—the passageway of the tubular section 106 of cylindrical body of the syringe 100. The lower press head 110 of the piston 108 preferably slides in abutment with the surface of the passageway of the tubular section 106 so as to push any matter contained within the interior passageway toward the tip 102 when a force is applied to the handle 112 pushing the piston 108 to a further extent within the passageway, whereby matter contained within the passageway may be expelled through a distal opening in the tip 102.

The funnel-shaped top 104 and tubular section 106 preferably consist of a single molded piece to which the tip 102 is removably attachable in threaded engagement by screwing the tip 202 onto a lower threaded end portion of the body of the syringe 100. Additionally, the single molded piece preferably is transparent, as shown in FIG. 1. The tip 102 also may be transparent as shown in FIG. 1, or the tip may be opaque. In a variation, the body—including the tip—consists of a single molded piece. Similarly, the piston preferably consists of a single molded piece.

In use, the syringe 100 preferably is filled with bone for delivery to a patient during surgery. The bone preferably is autologous bone. In particular, the passageway of the tubular section 106 of the body of the syringe 100 is at least partially filled with the bone by inserting the bone through the funnel-shaped top 104. The plunger then is inserted through the funnel-shaped top 104 to extend within the passageway of the tubular section 106. As the plunger is further inserted, the press head 110 at the lower end of the piston 108 engages and pushes the bone toward the tip 102, and the plunger eventually reaches an extent at which further pushing will begin expelling the bone through the opening in the tip 102. The syringe 100 then can be used to deliver bone to the patient during surgery by placing the tip 102 at the desired location relative to the patient and pushing on the handle 112 to further extend the plunger within the body of the syringe 100.

Figure 7B:
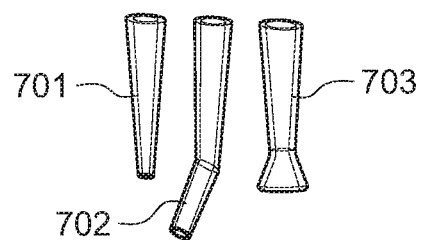
Figure 7A:
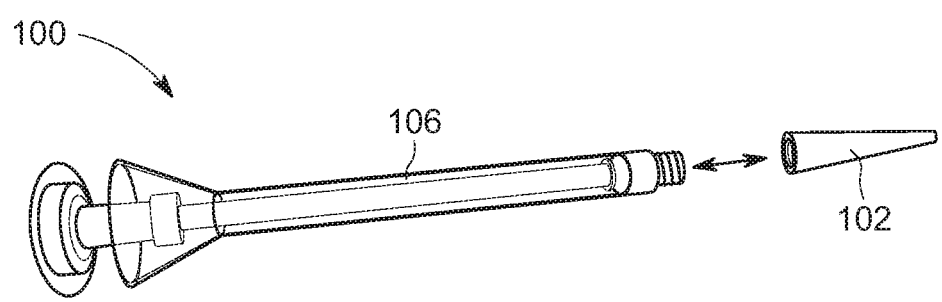
FIG. 7a is a perspective view of apparatus for delivery of bone in accordance with the first embodiment of the present invention, and illustrates the feature of a tip being removable from the body of the syringe via a threaded engagement.

In addition to the foregoing, FIG. 7a is a perspective view of apparatus for delivery of bone in accordance with the first embodiment of the present invention, and illustrates the feature of a tip 102 being removable from the body of the syringe 100 via a threaded engagement. Furthermore, additional tips 701, 702, 703 that are interchangeable—each being configured to be screwed onto the tubular section 106 of the syringe 100—are shown in perspective view in FIG. 7b. Each of the tips 701, 702, 703 includes a different profile for different flow delivery of bone when the syringe 100 is used. With further regard to a plurality of interchangeable tips, one or more preferred kits in accordance with one or more aspects and features of the present invention includes a syringe body and a plurality of interchangeable tips compatible with the syringe body, each having a different profile for providing a different flow delivery when used.

Figure 8A:
FIGS. 8a, 8b, and 8c collectively illustrate flexibility and elasticity characteristics of a tip in accordance with one or more aspects and features of the present invention.
Figure 8B:
Figure 8C:
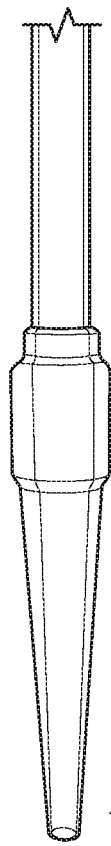
Figure 9A:
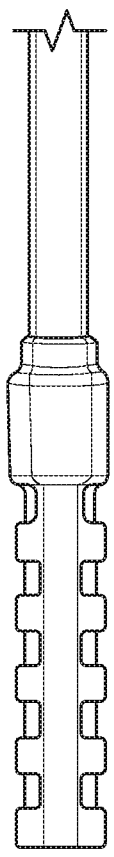
FIGS. 9a, 9b, and 9c collectively illustrate a flexibility without elasticity characteristic of a tip in accordance with one or more aspects and features of the present invention.
Figure 9B:
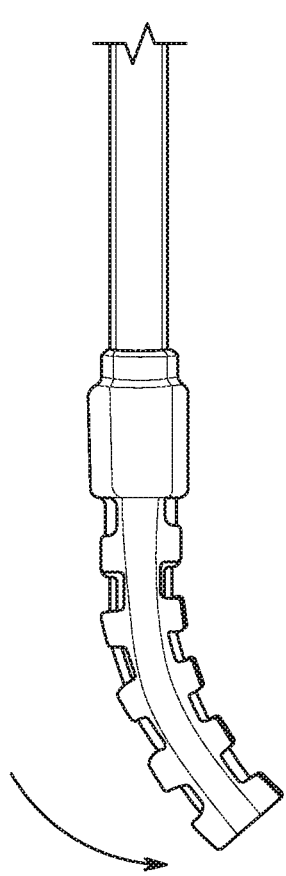
Figure 9C:
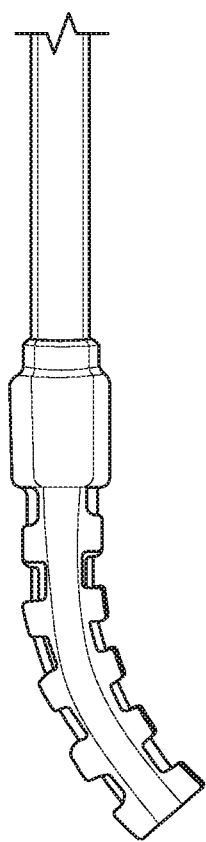

Additionally, a tip may be flexible and elastic, the tip self-returning to an initial position after deflection or bending; such flexibility and elasticity is illustrated, for example, in FIGS. 8a-8c. Alternatively, a tip may be flexible but not elastic and thus may remain in a deflected or bent position without self-returning; such alternative is illustrated, for example, in FIGS. 9a-9c.

Figure 12:
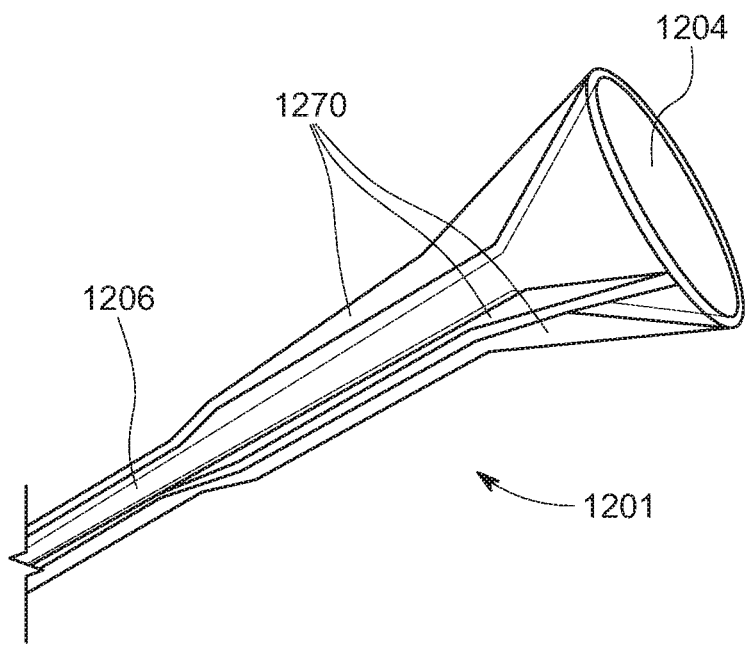
FIG. 12 is a perspective view of a portion of syringe body in accordance with one or more aspects and features of the invention.
Figure 13A:
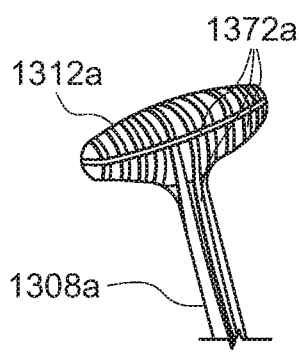
Figure 13B:
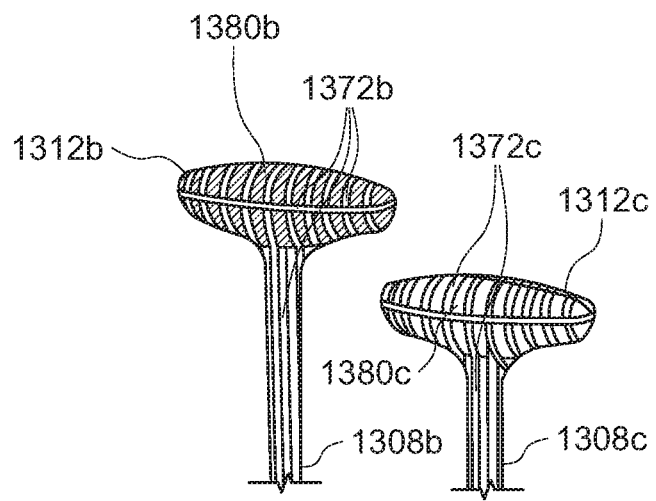

A perspective view of a portion of syringe body 1201 is shown in FIG. 12 and serves to illustrate three ribs 1270 that are provided for increasing the rigidity and structural integrity of the syringe body 1201 when force is applied to a plunger pushing matter contained in the syringe body 1201 out through a tip of the syringe. Three ribs 1270 are shown in FIG. 12, and extend from the funnel-shaped top 1204 down to and along an upper portion of the tubular section 1206. The ribs 1270 together with at least the funnel-shaped top 1204 and the tubular section 1206 preferably consist of a single molded piece.

Various alternative handles to the handle 112 are shown in FIGS. 13a through 18b. In this respect, handles 1312a, 1312b, 1312c shown in FIGS. 13a and 13b include structural ribs 1372a, 1372b, 1372c respectively that are formed as part of both the handle 1312a, 1312b, 1312c and the piston 1308a, 1308b, 1308c. These structural ribs are provided in the handle 1312 and piston 1308 for increasing the rigidity and structural integrity of the plunger when force is applied thereto pushing matter contained in a syringe body out through a tip thereof. One or more thermoplastic elastomers (TPEs) 1380c, 1380c, sometimes referred to as thermoplastic rubbers, can be molded between or over the ribbed structure for added comfort, as shown in the handles 1312b and 1312c of FIG. 13b.

Figure 14:
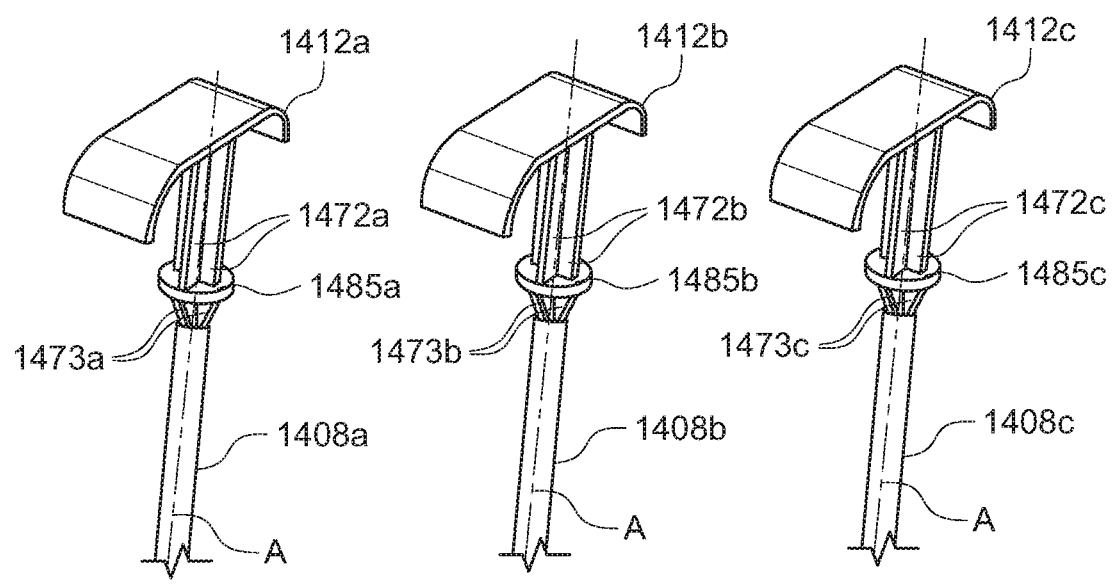
Figure 16A:
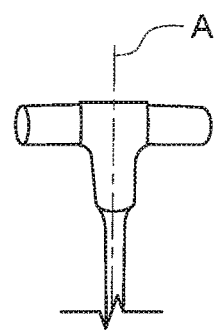
Figure 16B:
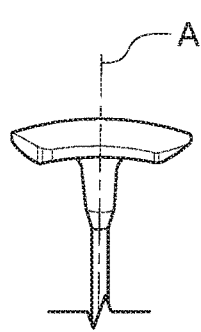
Figure 16C:
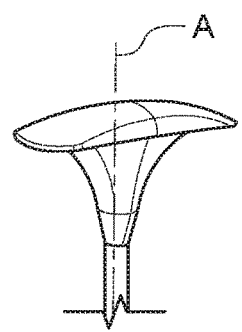
Figure 16D:
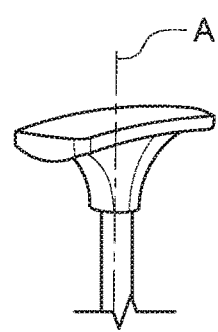
Figure 16E:
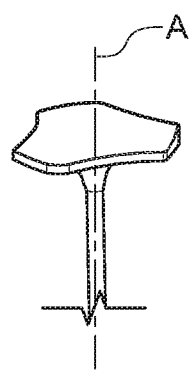
Figure 16F:
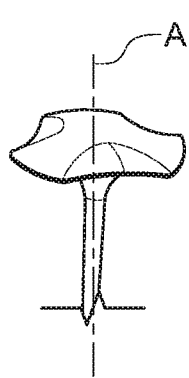
Figure 16G:
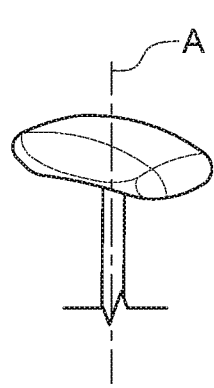
Figure 16H:
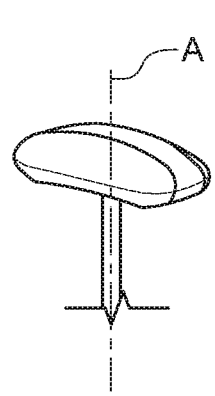

FIG. 14 is a perspective view of the upper portions of three similarly constructed plungers including handles 1412a, 1412b, 1412c and pistons 1408a, 1408b, 1408c. Each handle is generally offset radially from an axis A of the respective piston 1408a, 1408b, 1408c. Ribs 1472a, 1472b, 1472c are provided along the respective piston 1408a, 1408b, 1408c between the handle and a annular flange section 1485a, 1485b, 1485c of the piston 1408a, 1408b, 1408c. The annular flange section 1485a, 1485b, 1485c preferably mates with an interior circumferential perimeter of a funnel-shaped top of a syringe body with which the plunger is used. Ribs 1473a, 1473b, 1473c extending from the annular flange section 1485a, 1485b, 1485c away from the handle preferably extend at an angle matching that of the inside funnel-shaped surface of the syringe body with which the plunger is used for abutting fit therewith. The annular flange section 1485a, 1485b, 1485c and surface defined by the upper edges of the ribs 1473a, 1473b, 1473c thereby define a physical stop against extension of the plunger within the passageway of the syringe body.

Each of FIGS. 15a, 15b, 15c illustrate perspective views of a handle 1512a, 1512b, 1512c defining one or more openings 1513a, 1513b, 1513c each for receiving one or more digits of a hand when the handle is grasped. The one or more openings 1513a, 1513b, 1513c are entirely enclosed by the handle 1512a, 1512b, 1512c. The handle thereby protects a user's knuckles from contacting the funnel-shaped top of a syringe during use.

Still yet additional perspective views of handles of plungers are shown in FIGS. 16a through 16h. Each preferably is symmetrical about an axis A of the piston shown therewith.

Figure 17A:
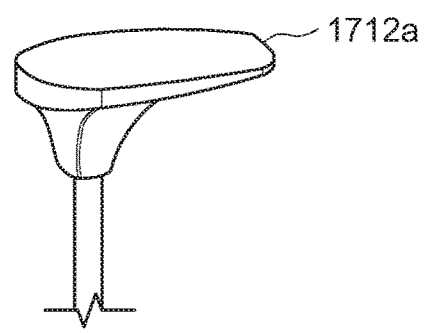

A perspective view of a handle 1712a of a plunger is shown in FIG. 17a. The handle is offset from a longitudinal axis of the piston, as shown. The handle 1712a includes a top flat surface and is believed to accommodate use of a mallet, if needed, when pushing bone through and out of the syringe body with which the plunger is used.

Figure 17B:
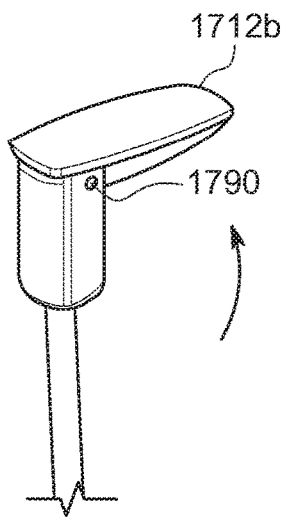
Figure 17C:
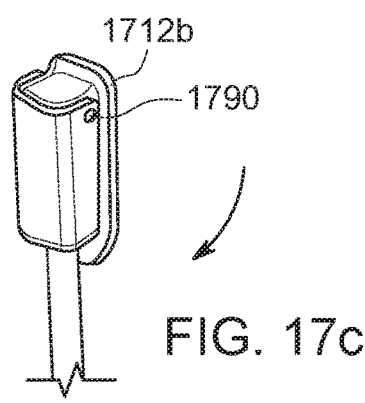

A perspective view of a handle 1712b of a plunger is shown in FIG. 17b and FIG. 17b. The handle 1712b includes a pin 1790 about which a top portion of the handle is connected to a bottom portion of the handle and pivots relative thereto, as illustrated by the arrows in FIGS. 17b and 17c. The handle thus is transitionable between a use configuration and a folded configuration in which increased space economy is achieved.

Figure 18A:
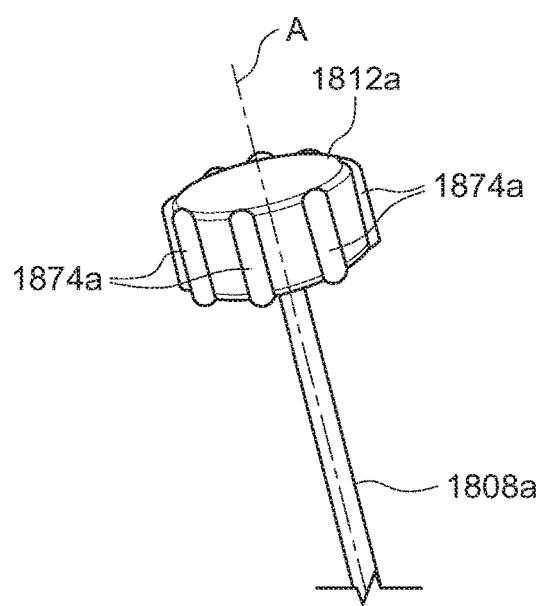
Figure 18B:
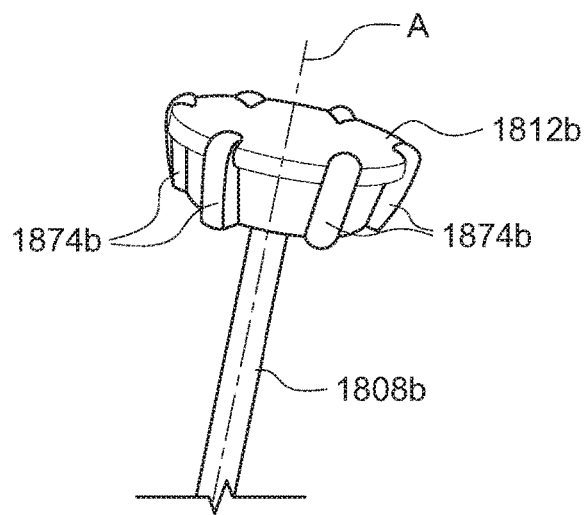

A perspective view of a handle 1812a of a plunger that is knobbed shaped is shown in FIG. 18a, and a perspective view of another handle 1812b of a plunger that also is knobbed shaped is shown in FIG. 18b. Each includes side ribs 1874a, 1874b for increased gripping effectiveness when the handle is gripped and the plunger used. The ribs 1874a, 1874b extend along the circumferential sides thereof in a direction generally parallel to a longitudinal axis A of the piston 1808a, 1808b.

It will be appreciated that, with respect to the handles shown in FIGS. 16a-18b, the handles preferably are not integrally formed with the piston but, instead, are attached to the upper end of the piston after being made. The attachment may be a threaded engagement; a friction fit; bonded or adhered using a bonding element, such as glue or other adhesive; or other conventional mechanism or manner for attachment of such components.

A Second Embodiment

Figure 2:
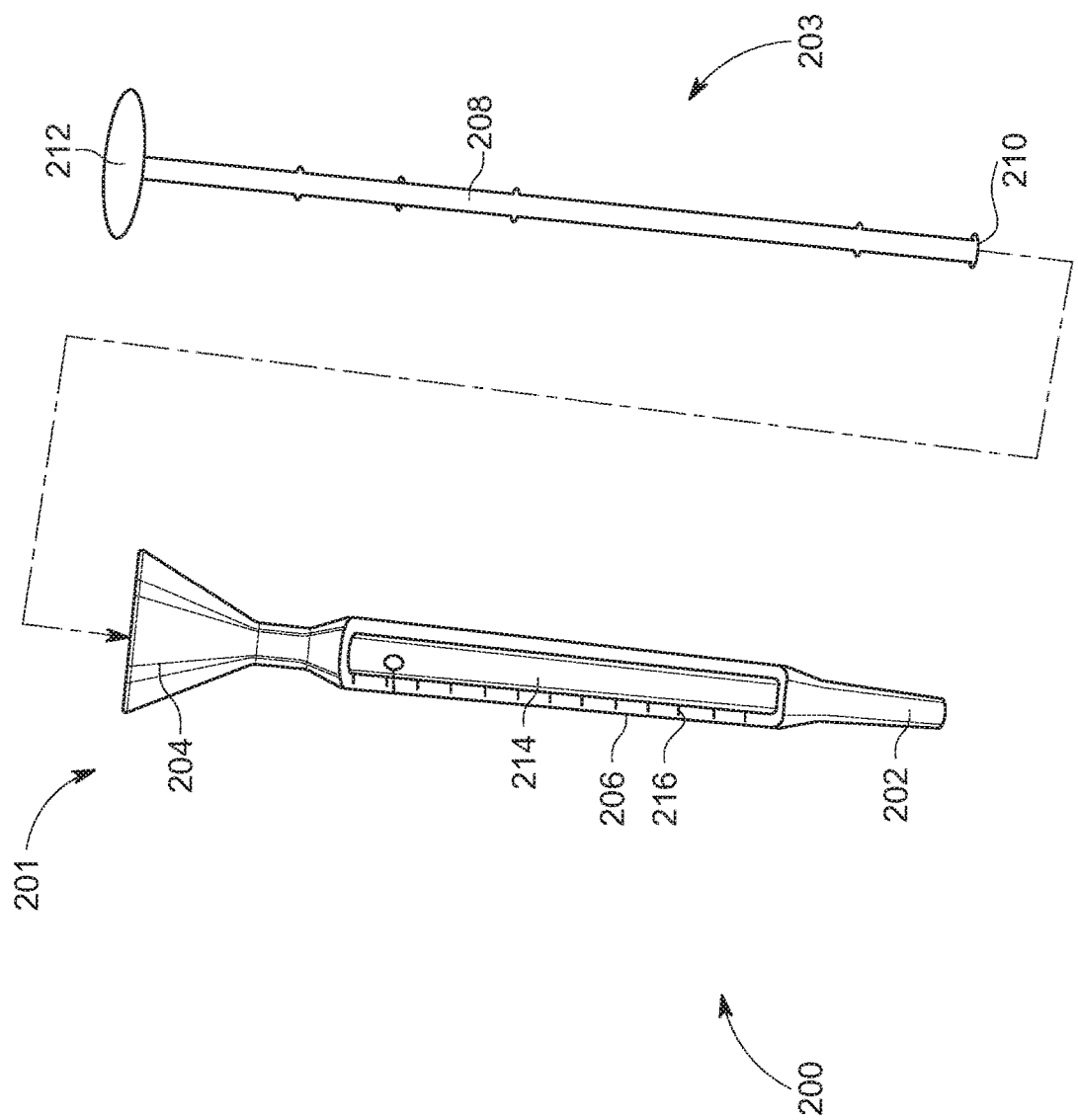
FIG. 2 is a perspective view of an apparatus for delivery of bone in accordance with a second embodiment of the present invention, wherein the apparatus comprises a syringe 200.

A perspective view of an apparatus for delivery of bone in accordance with a second embodiment of the present invention is shown in FIG. 2 and comprises a syringe 200. The syringe 200 comprises a body 201 including a tip 202 at a bottom thereof, a funnel-shaped top 204, and a tubular section 206 with a generally cylindrical interior wall defining a passageway extending from the funnel-shaped top 204 to the tip 202.

The syringe 200 further comprises a plunger 203 comprising an elongate piston 208. The plunger 203 further comprises a press head 210 and a handle 212, with the piston 208 extending between the press head 210 at a lower end thereof and the handle 212 at an upper end thereof.

The piston 208 is dimensioned to be received through the funnel-shaped top 204 into—and extend within—the passageway of the tubular section 206 of the body 201 of the syringe 200. The lower press head 210 of the piston 208 preferably slides in abutment with the wall defining the passageway of the tubular section 206 so as to push any matter contained within the interior space toward the tip 202 when a force is applied to the handle 212 pushing the piston 208 to a further extent within the interior space. Matter contained within the interior space thereby is expelled through a distal opening in the tip 202.

The funnel-shaped top 204 and tubular section 206 preferably consist of a single molded piece, to which the tip 202 is removably attachable in a threaded engagement by screwing the tip 202 onto a lower end portion of the tubular section 206. In a variation, the funnel-shaped top 204, the tubular section 206, and the tip 202 consist of a single molded piece.

As shown in FIG. 2, the syringe 200 further comprises a transparent window 214 extending within an opening defined in the tubular section 206, which window extends along a length of the tubular section 206 between the funnel-shaped top 204 and tip 202. Matter that is contained within the interior space is viewable through the window 214. Moreover, graduations 216 are provided along the extent of the tubular section 206 adjacent the window 214 by which matter contained within the interior space may be measured for delivery. The graduations 216 preferably are equally spaced in linear sequence along the window 214 and are oriented in generally parallel relation to each other. The graduations 216 may be formed in the tubular section 206 itself by, for example, providing indentions or raised areas. Alternatively, or in addition thereto, the graduations 216 may be defined by coloring or other markings made on the surface of the tubular section 206.

The tip 202 may be transparent or the tip may be opaque.

In use, the syringe 200 preferably is filled with bone for delivery to a patient during surgery. The bone preferably is autologous bone. In particular, the passageway of the tubular section 206 of the syringe 200 is at least partially filled with the bone by inserting the bone through the funnel-shaped top 204. The plunger 203 then is inserted through the funnel-shaped top 204 to extend within the passageway of the tubular section 206. As the plunger 203 is further inserted, the press head 210 at the lower end of the piston 208 engages and pushes the bone toward the tip 202, and the plunger 203 eventually reaches an extent at which further pushing will begin expelling the bone through the opening in the tip 202. The syringe 200 then can be used to deliver bone to the patient during surgery by placing the tip 202 at the desired location relative to the patient and pushing on the handle 212 to further extend the plunger 203 within the body of the syringe 200.

Additionally, the amount of bone delivered can be measured by reading the graduations 216 provided adjacent the transparent window 214.

A Third Embodiment

Figure 3:
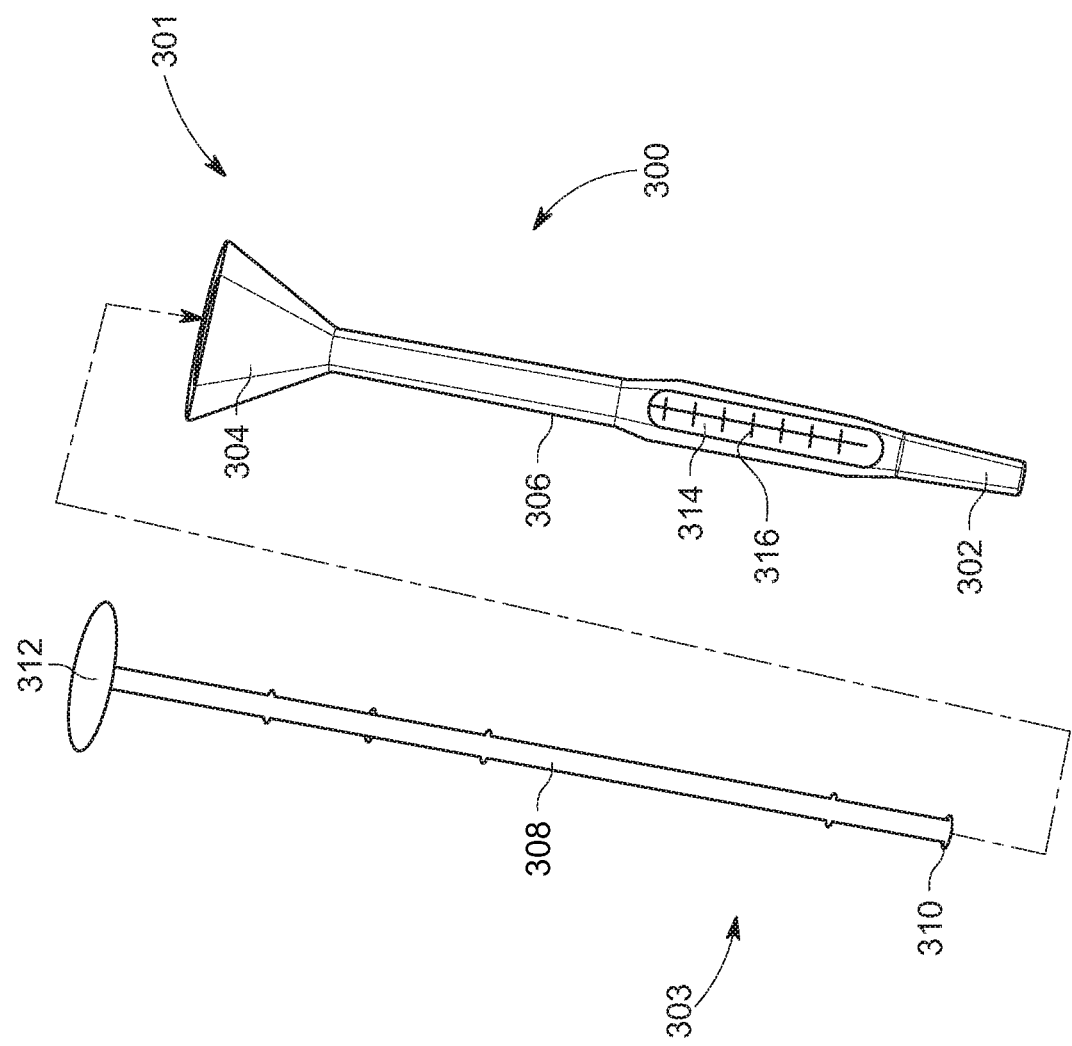
FIG. 3 is a perspective view of an apparatus for delivery of bone in accordance with a third embodiment of the present invention, wherein the apparatus comprises a syringe 300.

A perspective view of an apparatus for delivery of bone in accordance with a third embodiment of the present invention is shown in FIG. 3 and comprises a syringe 300. The syringe 300 comprises a body 301 including a tip 302 at a bottom thereof, a funnel-shaped top 304, and a tubular section 306 with a generally cylindrical interior wall defining a passageway extending from the funnel-shaped top 304 to the tip 302.

The syringe 300 further comprises a plunger 303 comprising an elongate piston 308. The plunger 303 further comprises a press head 310 and a handle 312, with the piston 238 extending between the press head 310 at a lower end thereof and the handle 312 at an upper end thereof.

The piston 308 is dimensioned to be received through the funnel-shaped top 304 into—and extend within—the passageway of the tubular section 306 of the syringe 300. The lower press head 310 of the piston 308 preferably slides in abutment with the wall defining the passageway of the tubular section 306 so as to push any matter contained within the passageway toward the tip 302 when a force is applied to the handle 312 pushing the piston 308 to a further extent within the passageway. Matter contained within the passageway thereby is expelled through a distal opening in the tip 302.

The funnel-shaped top 304 and the tubular section 306 preferably consist of a single molded piece, to which the tip 302 is removably attachable in a threaded engagement by screwing the tip 302 onto a lower end portion of the tubular section 306. In a variation, the funnel-shaped top 304, the tubular section 306, and the tip 302 consist of a single molded piece.

As shown in FIG. 3, the syringe 300 further comprises a transparent window 314 extending within an opening defined in the tubular section 306, which window extends along a length of a lower half of the tubular section 306. Matter that is contained within the interior space is viewable through the window 314. Moreover, graduations 316 are provided along the extent of the window 314 on the window 314 itself, by which matter contained within the interior space may be measured for delivery. The graduations 316 preferably are equally spaced in linear sequence along the window 314 and are oriented in generally parallel relation to each other. The graduations 316 may be formed in the window 314 itself by, for example, providing indentions or raised areas therein. Alternatively, or in addition thereto, the graduations 316 may be defined by coloring or other markings made on an interior or exterior surface of the window 314.

The tip 302 may be transparent or the tip may be opaque.

In use, the syringe 300 preferably is filled with bone for delivery to a patient during surgery. The bone preferably is autologous bone. In particular, the passageway of the tubular section 306 of the syringe 300 is at least partially filled with the bone by inserting the bone through the funnel-shaped top 304. The plunger 303 then is inserted through the funnel-shaped top 304 to extend within the passageway of the tubular section 306. As the plunger 303 is further inserted, the press head 310 at the lower end of the piston 308 engages and pushes the bone toward the tip 302, and the plunger 303 eventually reaches an extent at which further pushing will begin expelling the bone through the opening in the tip 302.

The syringe 300 then can be used to deliver bone to the patient during surgery by placing the tip 302 at the desired location relative to the patient and pushing on the handle 312 to further extend the plunger 303 within the body of the syringe 300.

Additionally, the amount of bone delivered can be measured by reading the graduations 316 provided adjacent the transparent window 314.

A Fourth Embodiment

Figure 4:
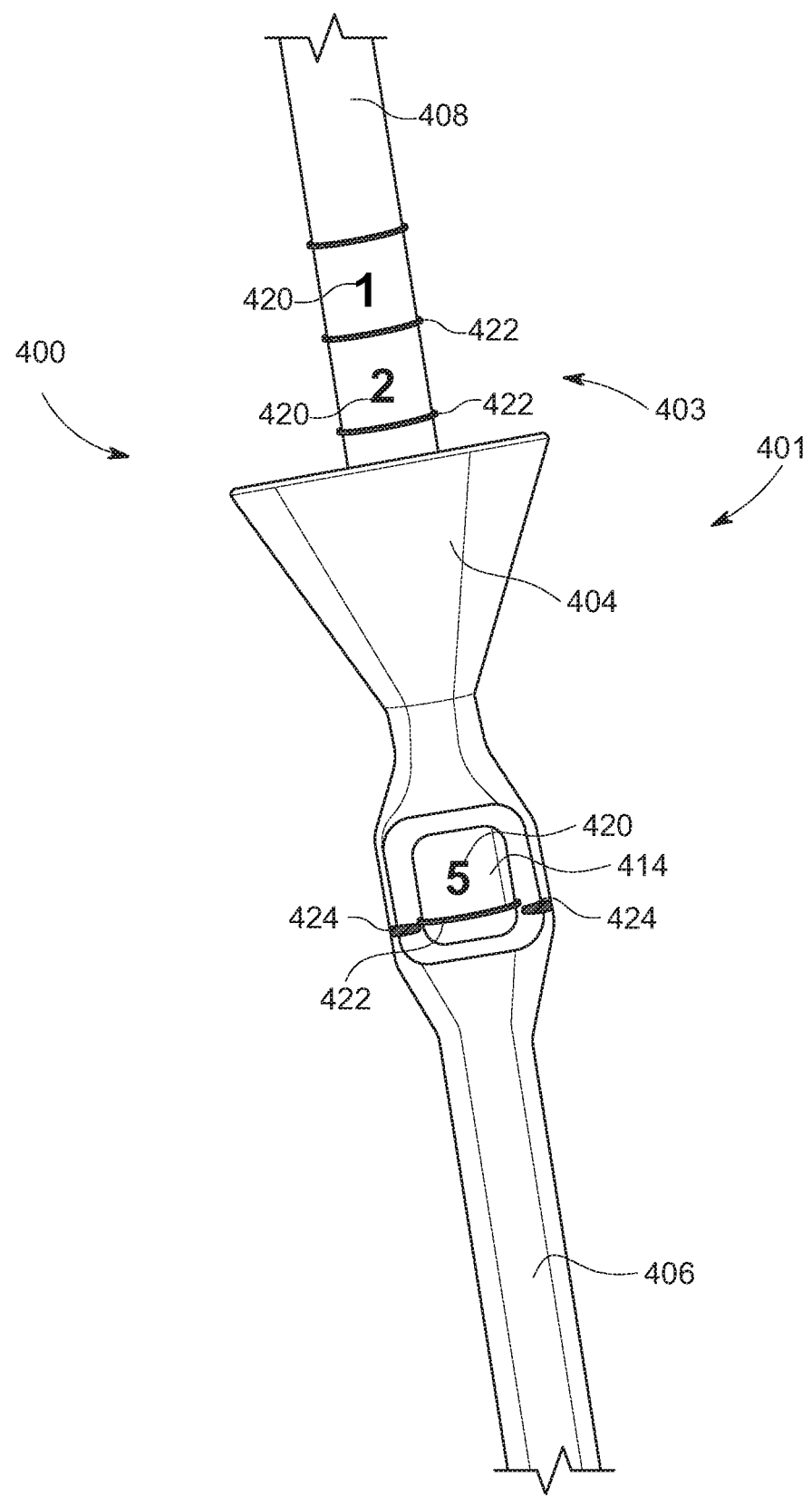
FIG. 4 is a partial, perspective view of an apparatus for delivery of bone in accordance with a fourth embodiment of the present invention, wherein the apparatus comprises a syringe 400.

FIG. 4 is a partial, perspective view of an apparatus for delivery of bone in accordance with a fourth embodiment of the present invention. The apparatus represented by FIG. 4 comprises a syringe 400 comprising a body 401 including a funnel-shaped top 404 and a tubular section 406 with a generally cylindrical interior wall defining a passageway extending from the funnel-shaped top 404 to a tip (not shown). The syringe 400 further comprises a plunger 403 comprising an elongate piston 408. The piston 408 is dimensioned to be received through the funnel-shaped top 404 into—and extend within—the passageway of the tubular section 406 of the body 401 of the syringe 400, as shown in FIG. 4. The plunger 408 further comprises a lower end press head for engaging matter contained within the syringe and a handle (not shown), as will be understood from the embodiments described above. The lower press head of the piston 408 preferably slides in abutment with the wall defining the passageway of the tubular section 406 of the body 401 so as to push any matter contained within the interior space toward the tip of the syringe when a force is applied to the handle pushing the piston 408 to a further extent within the interior space. Matter contained within the interior space thereby is expelled through a distal opening in the tip.

The funnel-shaped top 404 and tubular section 406 preferably consist of a single molded piece, to which the tip is removably attachable in a threaded engagement by screwing the tip onto a lower end portion of the tubular section 406. In a variation, the funnel-shaped top 404, the tubular section 406, and the tip consist of a single molded piece.

As shown in FIG. 4, the piston 408 includes numerical measurement indicators 420; those shown in FIG. 4 include "1", "2", and "5". The numerical measurement indicators 420 are separated by equally spaced, parallel line delineators 422. The syringe 400 further comprises a transparent window 414 extending within an opening defined in the tubular section 406, which window is located proximate the funnel-shaped top 404. Rather than being designed to view matter that is contained within the syringe, the window 14 is designed to show a single numerical measurement indicator 420 there through as found on the piston 408. Moreover, one or more alignment indicators 424 are provided on the tubular section 406, with which a delineator 422 on the piston 408 may be aligned when a corresponding numerical measurement indicator 420 is seen through the window 414, as shown in FIG. 4.

The indicators 420 may be formed in the piston 408 itself by, for example, providing indentions or raised areas therein. Alternatively, or in addition thereto, the indicators 420 may be defined by coloring or other markings made on the surface of the piston 408. Furthermore, the delineators 422 may be formed in the piston 408 itself by, for example, providing indentions or raised areas therein. Alternatively, or in addition thereto, the delineators 422 may be defined by coloring or other markings made on the surface of the piston 408. Similarly, the alignment indicators 424 may be formed in the tubular section 406 itself by, for example, providing indentions or raised areas therein. Alternatively, or in addition thereto, the alignment indicators 424 may be defined by coloring or other markings made on the surface of the tubular section 406.

In other embodiments, the alignment indicators are formed in the window itself by, for example, providing indentions or raised areas therein. Alternatively, or in addition thereto, the alignment indicators may be defined by coloring or other markings made on the interior or exterior surface of the window.

In use, the syringe 400 preferably is filled with bone for delivery to a patient during surgery. The bone preferably is autologous bone. In particular, the interior space defined by the tubular section 406 of the body 401 of the syringe 400 is at least partially filled with the bone by inserting the bone through the funnel-shaped top 404. The plunger 403 then is inserted through the funnel-shaped top 404 to extend within the passageway of tubular section 406. The amount of bone delivered can be measured by taking readings, each reading taken being of a numerical measurement indicator 420 as seen through the transparent window 414 when the corresponding delineator 422 aligns with the alignment indicators 422.

A Fifth Embodiment

Figure 5:
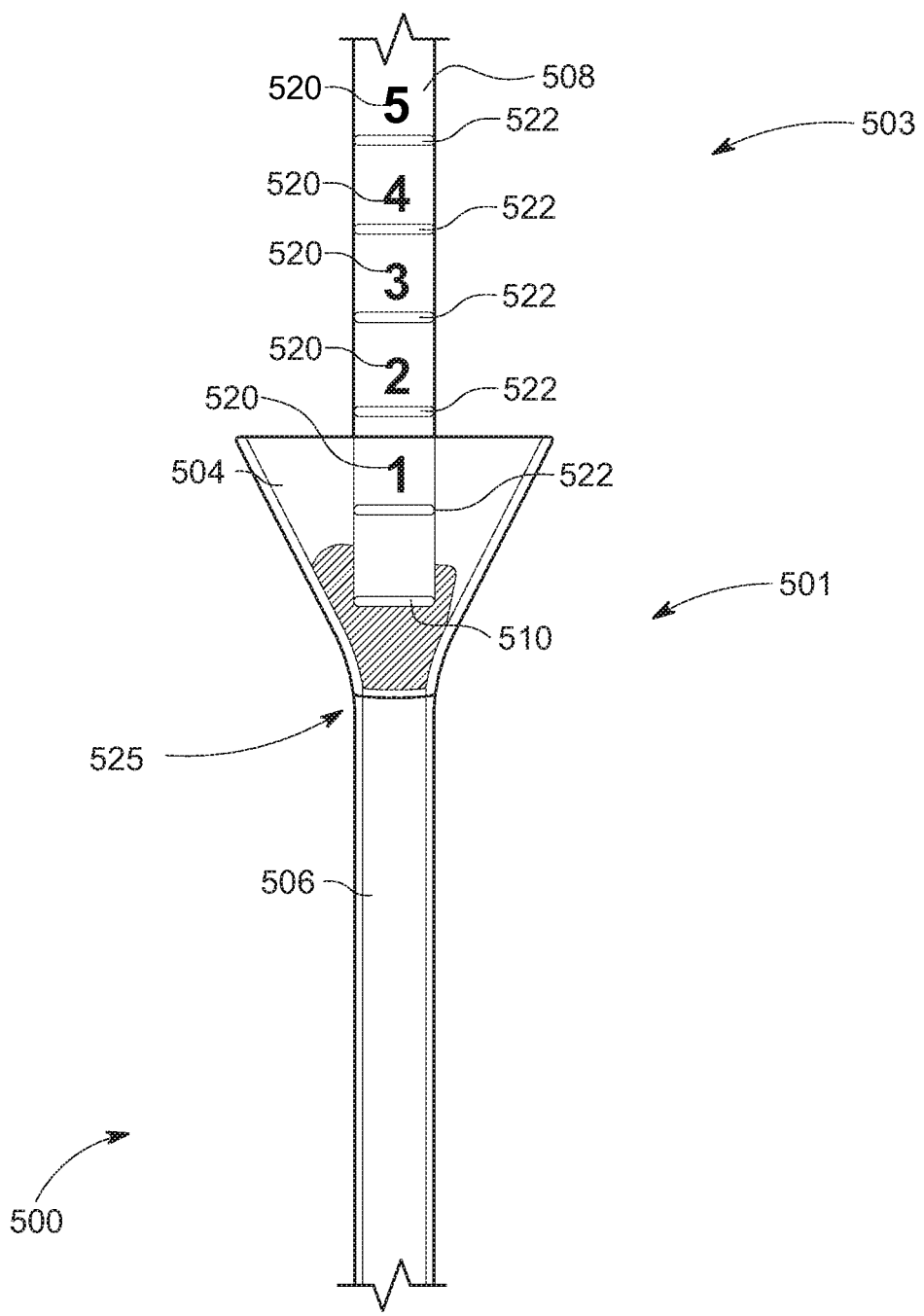
FIG. 5 is a partial, perspective view of an apparatus for delivery of bone in accordance with a fifth embodiment of the present invention, wherein the apparatus comprises a syringe 500.

FIG. 5 is a partial, perspective view of an apparatus for delivery of bone in accordance with a fifth embodiment of the present invention. The apparatus represented by FIG. 5 comprises a syringe 500 comprising a body 501 including a funnel-shaped top 504 and a tubular section 506 with a generally cylindrical interior wall defining a passageway extending from the funnel-shaped top 504 to a tip (not shown). The syringe 500 further comprises a plunger 503 comprising an elongate piston 508. The piston 508 is dimensioned to be received through the funnel-shaped top 504 into—and extend within—the passageway of the tubular section 506 of the body 501 of the syringe 500, as shown in FIG. 5. The plunger 508 further comprises a lower end press head 510 for engaging matter contained within the syringe and a handle (not shown), as will be understood from the embodiments described above. The lower press head 510 of the piston 508 preferably slides in abutment with the surface of the wall defining the passageway through the tubular section 506 so as to push any matter contained within the interior space toward the tip of the syringe when a force is applied to the handle pushing the piston 508 to a further extent within the interior space. Matter contained within the interior space thereby is expelled through a distal opening in the tip.

The funnel-shaped top 504 and tubular section 506 preferably consist of a single molded piece, to which the tip is removably attachable in a threaded engagement by screwing the tip onto a lower end portion of the tubular section 506. In a variation, the funnel-shaped top 504, the tubular section 506, and the tip consist of a single molded piece.

As shown in FIG. 5, the piston 508 includes numerical measurement indicators 520; those shown in FIG. 5 include "1", "2", "3", "4", and "5". The piston 508 includes equally spaced, parallel line delineators 522 corresponding to the numerical measurement indicators 520. The funnel-shaped top 504 of the syringe 500 further is transparent, enabling matter being packed into the passageway of the tubular section 506 to be seen, and enabling the indicators 520 and delineators 522 to be seen and read relative to the juncture (indicated at 525) between the funnel-shaped top 504 and the tubular section 506.

The indicators 520 may be formed in the piston 508 itself by, for example, providing indentions or raised areas therein. Alternatively, or in addition thereto, the indicators 520 may be defined by coloring or other markings made on the surface of the piston 508. Furthermore, the delineators 522 may be formed in the piston 508 itself by, for example, providing indentions or raised areas therein. Alternatively, or in addition thereto, the delineators 522 may be defined by coloring or other markings made on the surface of the piston 508.

In use, the syringe 500 preferably is filled with bone for delivery to a patient during surgery. The bone preferably is autologous bone. In particular, the passageway of the tubular section 506 of the syringe 500 is at least partially filled with the bone by inserting the bone through the funnel-shaped top 504. The plunger 503 then is inserted through the funnel-shaped top 504 to extend within the passageway of the tubular section 506. The amount of bone delivered can be measured by taking readings, each reading taken being of a numerical measurement indicator 520 and/or line delineator 522 as seen through the transparent top 504 when the corresponding delineator 422 aligns with the juncture 525 between the top 504 and the tubular section 506.

A Sixth Embodiment

Figure 6:
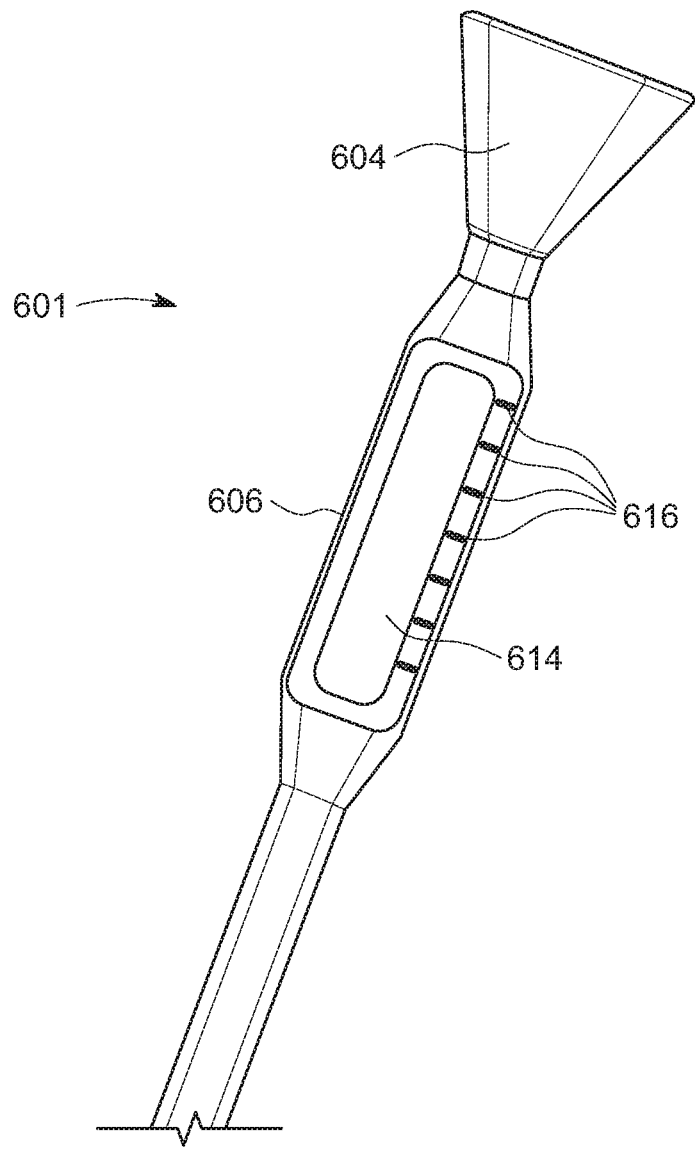
FIG. 6 is a partial, perspective view of a body of another syringe for delivery of bone in accordance with a sixth embodiment of the present invention.

FIG. 6 is a partial, perspective view of a body of another syringe for delivery of bone in accordance with a sixth embodiment of the present invention. The plunger is omitted in FIG. 6; however, it will be appreciated that the syringe is similar in construction and use to the syringe 300 of FIG. 3, with the one or more following notable exceptions.

With reference to FIG. 6, the a body 601 of the syringe includes a funnel-shaped top 604 and a tubular section 606 with a generally cylindrical interior wall defining a passageway extending from the funnel-shaped top 604 to a lower tip (not shown). Unlike the body 301 shown in FIG. 3, a transparent window 614 extends within an opening defined in the tubular section 606 that is located in an upper half of the tubular section 606. In contrast, the window 314 is located along a length of a lower half of tubular section 306. Matter that is contained within the interior space is viewable through the window 614. Moreover, graduations 616 are provided on the tubular body 606 along the extent of the window 614, by which matter contained within the interior space may be measured for delivery. The graduations 616 preferably are equally spaced in linear sequence along the extent of the window 614 and are oriented in generally parallel relation to each other. The graduations 616 may be formed in the tubular section 606 itself by, for example, providing indentions or raised areas therein. Alternatively, or in addition thereto, the graduations 616 may be defined by coloring or other markings made on an exterior surface of the tubular section 606.

In use, the interior space defined by the tubular section 606 preferably is filled with bone for delivery to a patient during surgery. The bone preferably is autologous bone. In particular, the passageway of the tubular section 606 is at least partially filled with the bone by inserting the bone through the funnel-shaped top 604 until the bone is visible within the window 614. A plunger then is inserted through the funnel-shaped top 604 to extend within the passageway of the tubular section 606. The amount of bone delivered can be measured by taking readings using the graduations 616 provided adjacent the transparent window 614.

A Seventh Embodiment

Each of FIGS. 10a and 10b illustrates a preferred embodiment of a method for loading a syringe for delivery of bone in accordance with one or more aspects and features of the invention. The syringe actually used in such method is represented by the syringe body 1001 shown in FIG. 10*a* and such representation encompasses any of the above disclosed syringes. The body 1001 includes a funnel-shaped top 1004, lower tip (represented in FIG. 10*b* but not shown in FIG. 10*a*), and a tubular section 1006 with a generally cylindrical interior wall defining a passageway extending therebetween. In accordance with the preferred method, the syringe is loaded with bone for delivery by loading a plurality of cartridges 1050 into the syringe body 1001. Specifically, the cartridges 1050 are stacked in generally axial alignment—one on top of the other—within the passageway of the tubular section 1006. Each cartridge 1050 comprises a tube 1052 having open ends, and bone 1054 is packed into each cartridge 1050 before the loading operation. The tube 1052 is generally cylindrical and includes an outer diameter generally corresponding to the inner diameter of the passageway of the tubular section 1006 so that a close fit is achieved between the tube 1052 and the generally cylindrical interior wall of the passageway of the tubular section 1006. The inner diameter of the tube 1052 of each cartridge 1050 preferably corresponds generally to the outer diameter of the plunger of the syringe such that the press head 1010 and piston 1008 may extend within and through the stacked cartridges 1050 for pushing the bone 1054 through the stacked tubes 1052 and out of the tip 1002 of the syringe body 1001, as represented in FIG. 10*b*. In this respect, the piston 1008 and press head 1010 are shown in a first position prior to being inserted within the tube 1052 of the uppermost cartridge 1050, and are shown in phantom in a second position in which the press head 1010 and piston 1008 have been pushed through the uppermost cartridge 1050 and extend within the tube 1052 of the next succeeding cartridge 1050.

An Eighth Embodiment

Figure 11:
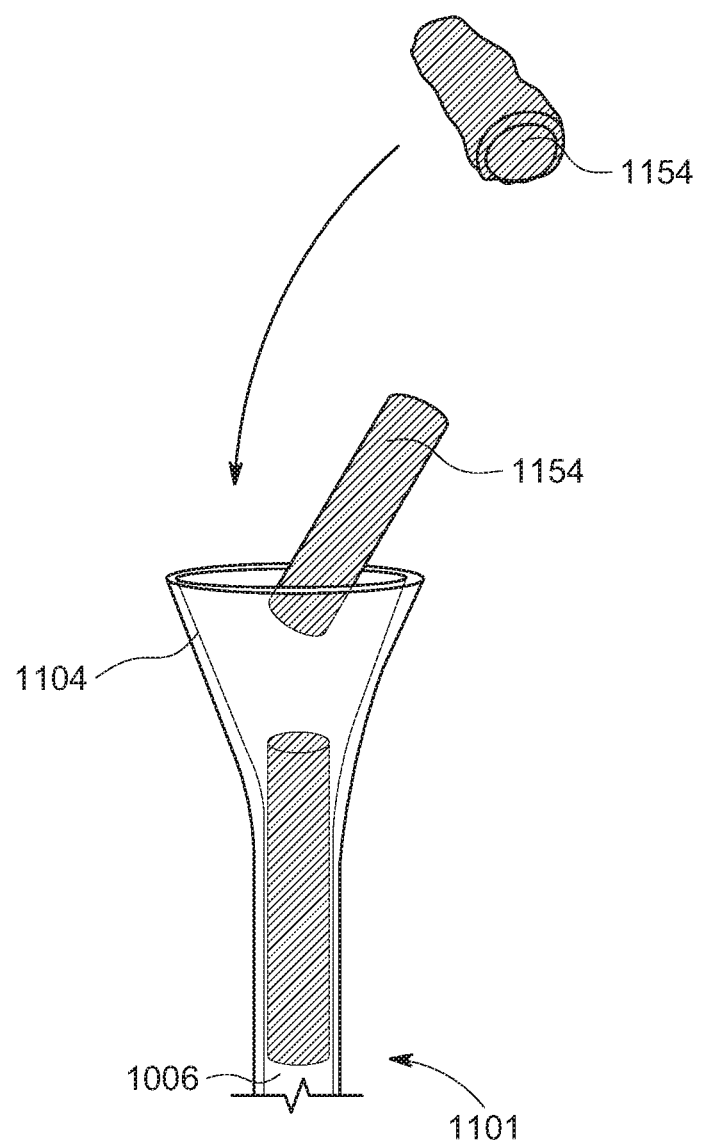
FIG. 11 illustrates another preferred embodiment of a method for loading a syringe for delivery of bone in accordance with one or more aspects and features of the invention.

FIG. 11 illustrates another preferred embodiment of a method for loading a syringe for delivery of bone in accordance with one or more aspects and features of the invention. The syringe actually used in such method is represented by the syringe body 1101 shown in FIG. 11, and such representation encompasses any of the above disclosed syringes. The body 1101 includes a funnel-shaped top 1104, lower tip (not shown), and a tubular section 1106 having a generally cylindrical wall defining a passageway extending therebetween. In accordance with the preferred method, the syringe is loaded with bone for delivery by loading separate pre-formed bone pellets 1154, each having a generally cylindrical shape. Preferably, each pellet 1154 represents bone that has been pressed to form its generally cylindrical shape using a clamshell molding press. The outer diameter of each pellet 1154 generally corresponds to the inner diameter of the passageway of the tubular section 1106. Furthermore, the pellets 1154 are stacked in generally axial alignment—one on top of the other—within the passageway of the tubular section 1106.

A Ninth Embodiment

Figure 19:
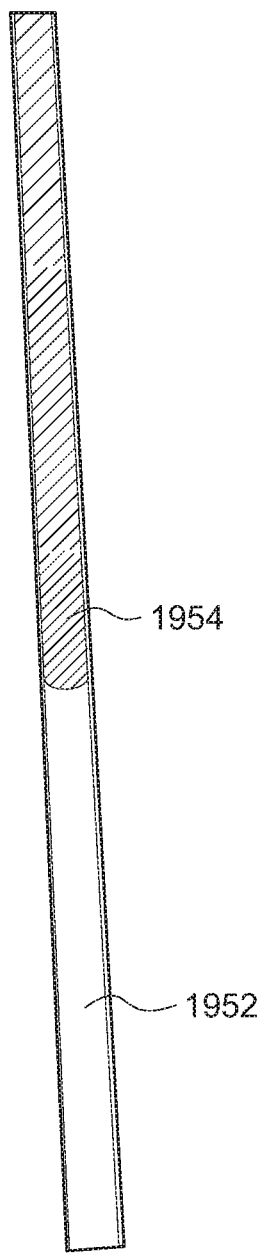
FIG. 19 is representative of another preferred embodiment of a method for loading a syringe for delivery of bone in accordance with one or more aspects and features of the invention, in which figure a perspective view of a cartridge is illustrated.

FIG. 19 is representative of another preferred embodiment of a method for loading a syringe for delivery of bone in accordance with one or more aspects and features of the invention. The syringe used in such method may be any of the syringes described above. In accordance with this method, a single cartridge is used to fully load the interior space of a tubular section of a syringe, as opposed to multiple cartridges. The single cartridge preferably comprises a rigid tube 1952 having a curved cross-section generally matching that of the generally cylindrical interior wall of the passageway of the tubular section of a syringe with which the tube 1952 is used. In this regard, the outer diameter of the tube 1952 generally corresponds to the inner diameter of the generally cylindrical interior wall of the passageway, with the tube 1952 being slightly smaller such that the tube 1952 may be received in close fit with the generally cylindrical interior wall of the passageway. The single tube 1952 thereby lines the generally cylindrical interior wall of the passageway. Such a tube is schematically represented by a top plan view thereof in FIG. 20*a* with the curved cross-section thereof being schematically represented in FIG. 20*b*.

In use, the tube 1952 is filled with bone 1954 as illustrated by perspective view of the filled tube shown in FIG. 19. The tube 1952 of FIG. 19 is made of a metal or metal alloy. The length of the tube 1952 at least equals and preferably exceeds the length of the tubular section of the syringe such that the tube 1952 may be fully inserted into and received within the entire length of the passageway defined by the tubular section. The tube 1952 preferably is prefilled with an amount of bone such that the bone does not extend beyond the juncture of the tubular section and the funnel-shaped top when the tube 1952 is fully received within the passageway.

Furthermore, the tube 1952 at least extends to the juncture of the tubular section and the funnel-shaped top when the tube 1952 is fully received within the tubular section, and preferably slightly there beyond for presenting an extent thereof for insertion into and removal from the passageway by hand Once the tube 1952 is loaded, a plunger having an outer diameter generally corresponding to the inner diameter of the tube 1952 is used to push bone through the syringe and out of the tip of the syringe. Once emptied, the plunger is removed and the emptied tube 1952 is removed. Another, filled tube like tube 1952 may then be inserted into the passageway of the tubular section of the syringe without the need to take time to fill the emptied tube 1952. The plunger then is inserted into the newly loaded tube for continued bone delivery in an expedient manner. Preferably, at least three interchangeable tubes are present for loading/reloading, staging, and use during use in a medical procedure.

It will further be noted that a longitudinal opening 1956 extends the length of the tube 1952, as shown. Alternatively, the tube may be entirely enclosed circumferentially with no longitudinal opening (not shown). It is believed that providing a longitudinal opening facilitates radial (as opposed to longitudinal) placement and generally uniform packing of bone within the tube along the extent of the tube, avoiding packing by ramming with a plunger.

A Tenth Embodiment

Figures 21A, 21B:
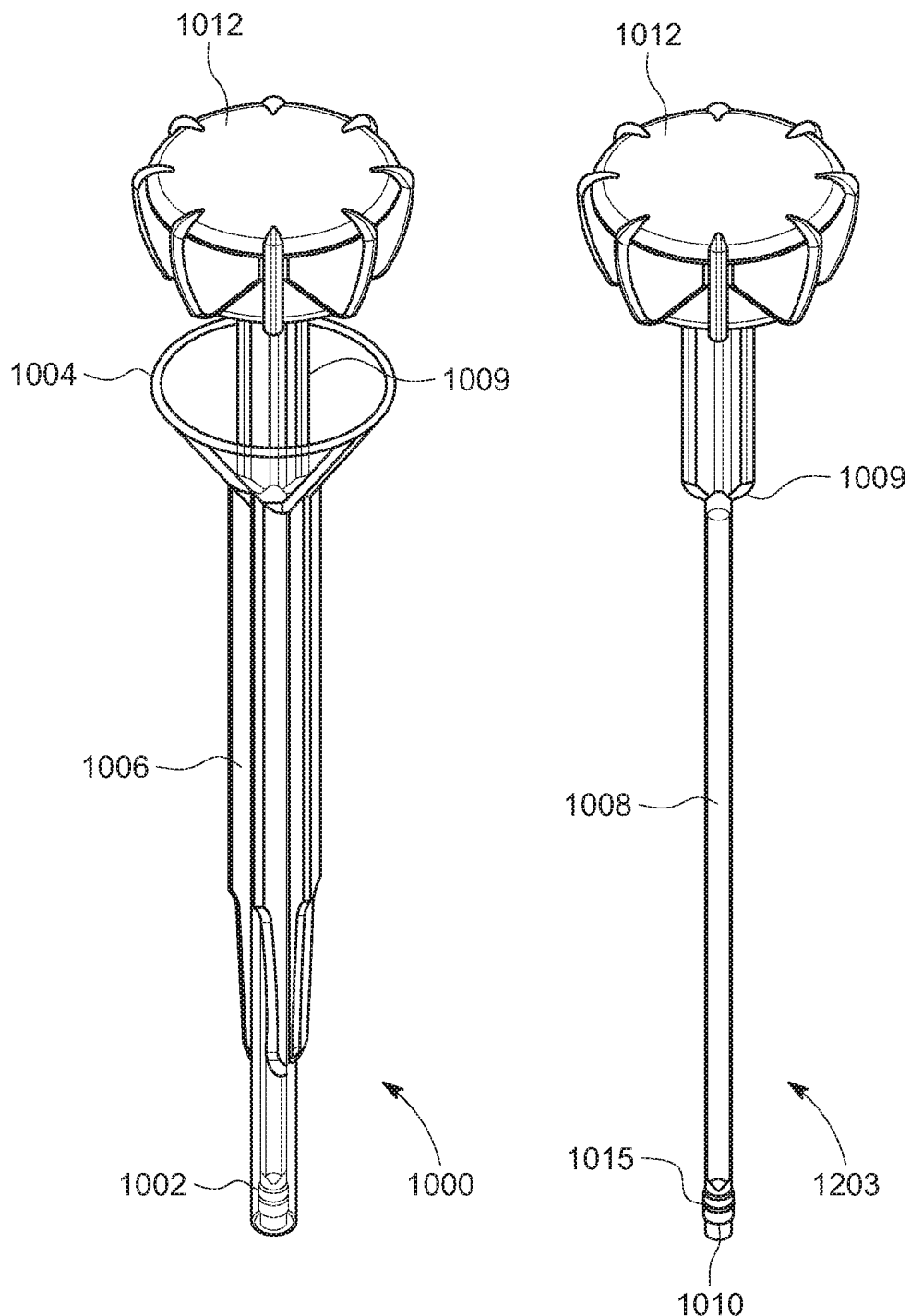

A perspective view of an apparatus for delivery of bone in accordance with a tenth embodiment of the present invention is shown in FIG. 21*a* and comprises a syringe 1000 comprising a tip 1002 at a bottom thereof, a funnel-shaped top 1004, and a tubular section 1006 with a generally cylindrical interior wall defining a passageway extending from the funnel-shaped top 1004 to the tip 1002. The syringe 1000 further comprises a plunger 1203 comprising an elongate piston 1008, a press head 1010 and a handle 1012, with the piston 1008 extending between the press head 1010 at a lower end thereof and the handle 1012 at an upper end thereof. The plunger 1203 is fully received within the tubular section 1006 in FIG. 21a. For clarity, the plunger 1203 is shown by itself in FIG. 21b.

In this illustrated embodiment, the tip 1002, the funnel-shaped top 1004, and the tubular section 1006 preferably are formed by a single piece of molded material, and the plunger 1203 preferably comprises a single piece of molded material.

The handle 1012 at the top of the plunger 1203 includes a large top surface area for pushing of the piston 1008 of the plunger 1203 through the passageway of the tubular section 1006 using the palm of a hand and, in turn, the press head 1010 pushes bone through the tubular section 1006 as the piston 1008 is pushed therethrough. The handle 1012 further extends longitudinally toward the press head 1010, which extent 1009 has a larger diameter than that of the piston 1008 and that of the passageway, whereby such extent 1009 of the handle 1012 acts as a stop to limit advancement of the piston 1008 through the passageway. A sealing ring 1015 further is shown located at the press head 1010 for sealing engagement with an interior surface of the passageway, whereby bone does not escape around the press head 1010 as it is pushed by the press head 1010 through the passageway.

An Eleventh Embodiment

A perspective view of an apparatus for delivery of bone in accordance with an eleventh embodiment of the present invention is shown in FIGS. 22a and 22b, and comprises a syringe 2000 comprising a tip 2002 at a bottom thereof, a funnel-shaped top 2004, and a tubular section 2006 with a generally cylindrical interior wall defining a passageway extending from the funnel-shaped top 2004 to the tip 2002. The syringe 2000 further comprises a plunger 2203 comprising an elongate piston 2008, a press head 2010 and a handle 2012, with the piston 2008 extending between the press head 2010 at a lower end thereof and the handle 2012 at an upper end thereof. The plunger 2203 is fully received within the tubular section 2006 in FIGS. 22a and 22b. For clarity, the plunger 2203 is shown by itself in FIG. 22c.

In this illustrated embodiment, the tip 2002, the funnel-shaped top 2004, and the tubular section 2006 preferably are formed by welding two individual pieces 2005a, 2005b of a molded material together. The seam between the pieces is perhaps best seen in the area of the funnel-shaped top at 2049 in FIG. 22a.

The plunger 2203 includes a collar 2019 through which the piston 2008 extends. The collar 2019 is positioned along the piston 2008 so as to limit advancement of the piston 2008 through the passageway beyond a predetermined extent. Preferably, the collar 2019 is held in frictional engagement with the piston 2008 and is adjustable up and down the piston 2008 by sliding upon application of sufficient force greater than that encountered when the collar 2019 engages the funnel-shaped top 2004 and acts as a stop. The piston 2008 preferably comprises a cylinder formed of a metal or metal alloy and is received within a bore of the handle 2012 in frictional fit therewith.

A Twelfth Embodiment

Figures 23A, 23B:
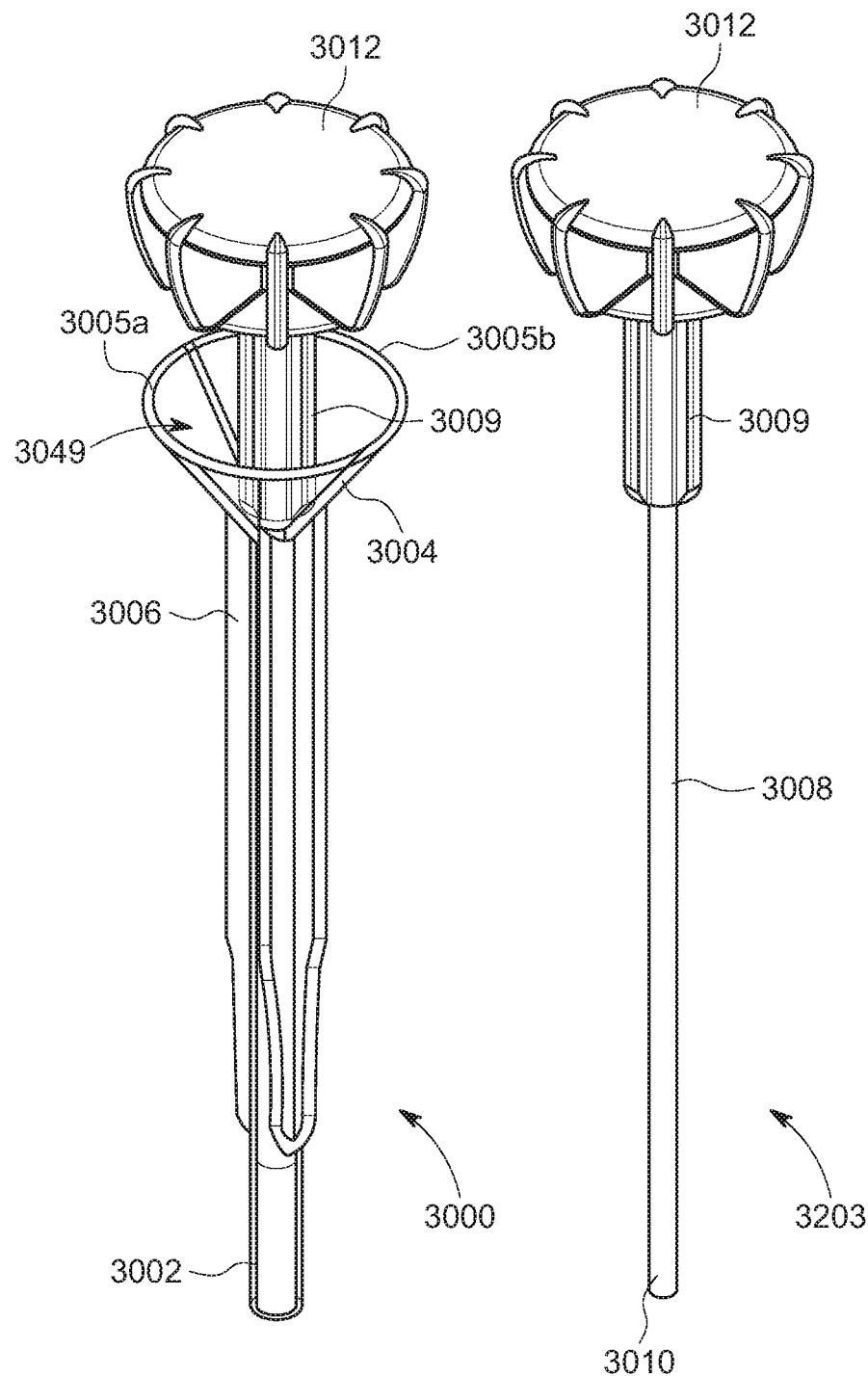
Figures 24A, 24B:
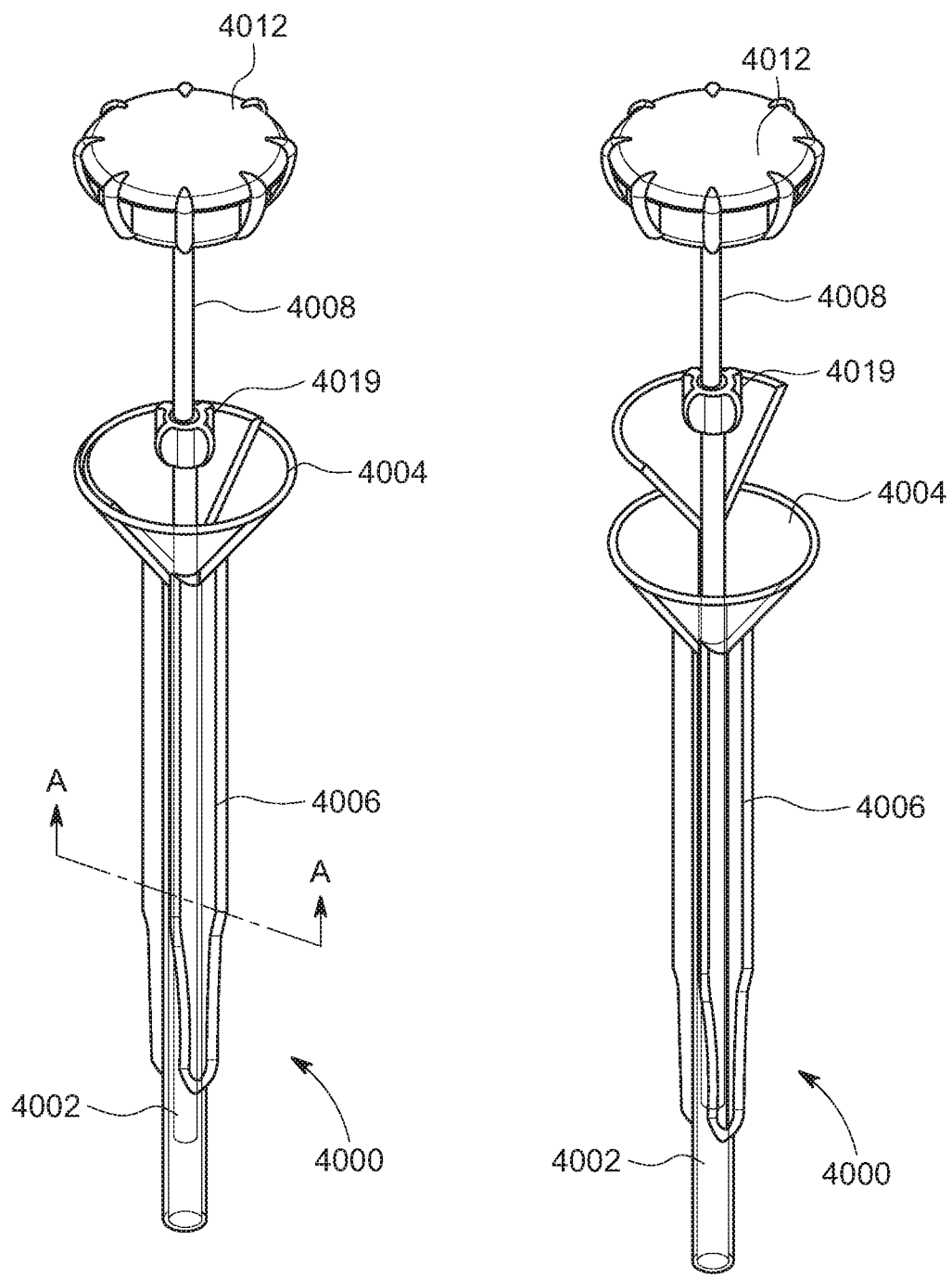
Figures 25A, 25B:
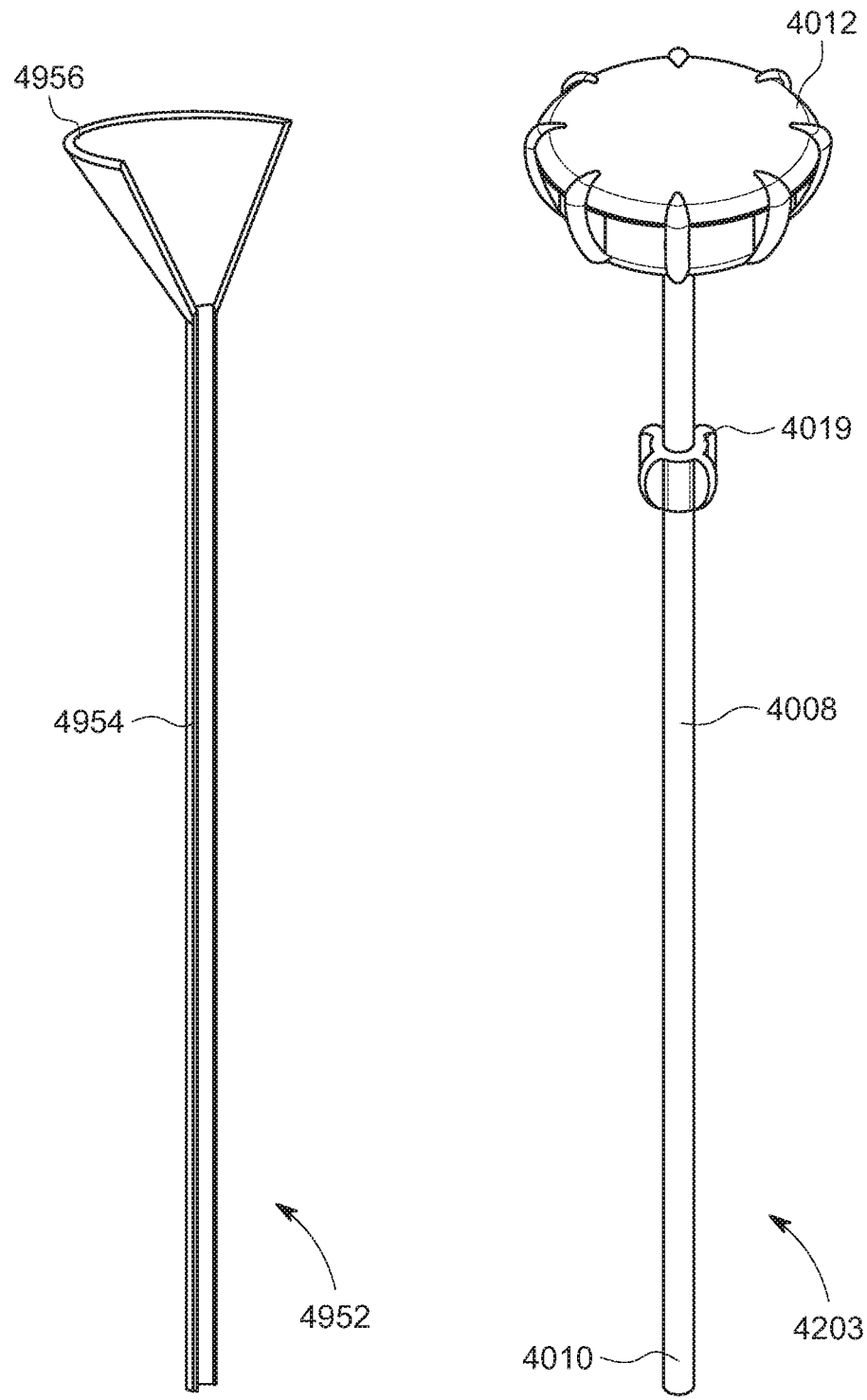

A perspective view of another apparatus for delivery of bone in accordance with a twelfth embodiment of the present invention is shown in FIGS. 23a and 23b, and comprises a syringe 3000 comprising a tip 3002 at a bottom thereof, a funnel-shaped top 3004, and a tubular section 3006 with a generally cylindrical interior wall defining a passageway extending from the funnel-shaped top 3004 to the tip 3002. The syringe 3000 further comprises a plunger 3203 comprising an elongate piston 3008, a press head 3010 and a handle 3012, with the piston 3008 extending between the press head 3010 at a lower end thereof and the handle 3012 at an upper end thereof. The plunger 3203 is fully received within the tubular section 3006 in FIG. 23a. For clarity, the plunger 3203 is shown by itself in FIG. 23b.

In this illustrated embodiment, the tip 3002, the funnel-shaped top 3004, and the tubular section 3006 preferably are formed by welding two individual pieces 3005a, 3005b of a molded material together. The seam between the pieces is perhaps best seen in the area of the funnel-shaped top at 3049 in FIG. 23a.

The handle 3012 at the top of the plunger 3203 includes a large top surface area for pushing of the piston 3008 of the plunger 3203 through the passageway of the tubular section 3006 using the palm of a hand and, in turn, the press head 3010 pushes bone through the tubular section 3006 as the piston 3008 is pushed therethrough. The handle 3012 further extends longitudinally toward the press head 3010, which extent 3009 has a larger diameter than that of the piston 3008 and that of the passageway, whereby such extent 3009 of the handle 3012 acts as a stop to limit advancement of the piston 3008 through the passageway. The piston 3008 preferably comprises a cylinder formed of a metal or metal alloy and is received within a receiving bore of the extent 3009 of the handle 3012 in frictional fit therewith.

A Thirteenth Embodiment

A perspective view of another apparatus for delivery of bone in accordance with a thirteenth embodiment of the present invention is shown in FIGS. 24a-26b, and comprises a syringe 4000 comprising a tip 4002 at a bottom thereof, a funnel-shaped top 4004, and a tubular section 4006 with a generally cylindrical interior wall defining a passageway extending from the funnel-shaped top 4004 to the tip 4002. The syringe 4000 further comprises a plunger 4203 comprising an elongate piston 4008, a press head 4010 and a handle 4012, with the piston 4008 extending between the press head 4010 at a lower end thereof and the handle 4012 at an upper end thereof. The plunger 4203 is shown by itself in FIG. 25b.

In this illustrated embodiment, the tip 4002, the funnel-shaped top 4004, and the tubular section 4006 preferably are formed by a single piece of molded material, and the plunger 4203 preferably comprises a single piece of molded material.

The plunger 4203 includes a collar 4019 through which the piston 4008 extends. The collar 4019 is positioned along the piston 4008 so as to limit advancement of the piston 4008 through the passageway beyond a predetermined extent. Preferably, the collar 4019 is held in frictional engagement with the piston 4008 and is adjustable up and down the piston 4008 by sliding upon application of sufficient force greater than that encountered when the collar 4019 engages the funnel-shaped top 4004 and acts as a stop. The piston 4008 preferably comprises a cylinder formed of a metal or metal alloy and is received within a bore of the handle 4012 in frictional fit therewith.

Additionally, this illustrated embodiment includes use of a cartridge 4952 that is prefilled with bone and then placed within the passageway of the tubular section 4006. The single cartridge 4952 is used to fully load the interior space of the tubular section 4006. The single cartridge 4952 as shown comprises a rigid, elongate shaft 4954 that is semi-circular in cross-section and that has a radius of curvature that generally matches the radius of curvature of the interior surface of the passageway of the tubular section 4006. In this regard, the outer diameter of the shaft 4954 generally corresponds to the inner diameter of the generally cylindrical interior wall of the passageway, with the shaft 4954 being slightly smaller such that the shaft 4954 may be received in close fit with the generally cylindrical interior wall of the passageway. The shaft 4954 of the cartridge 4952 thereby lines the generally cylindrical interior wall 4065 of the passageway. This is perhaps best seen in the cross-sectional view of FIG. 26b, which is taken along the line A-A of FIG. 24a.

The cartridge 4952 further includes a partial funnel-shaped top 4956 that corresponds to a portion of the funnel-shaped top 4004 of the syringe 4000. As illustrated, the partial funnel-shaped top 4956 corresponds to about half of the funnel-shaped top 4004, as perhaps best seen in the comparison and contrast of FIG. 24a with FIGS. 24b and 26a.

A Fourteenth Embodiment

Figure 27A:
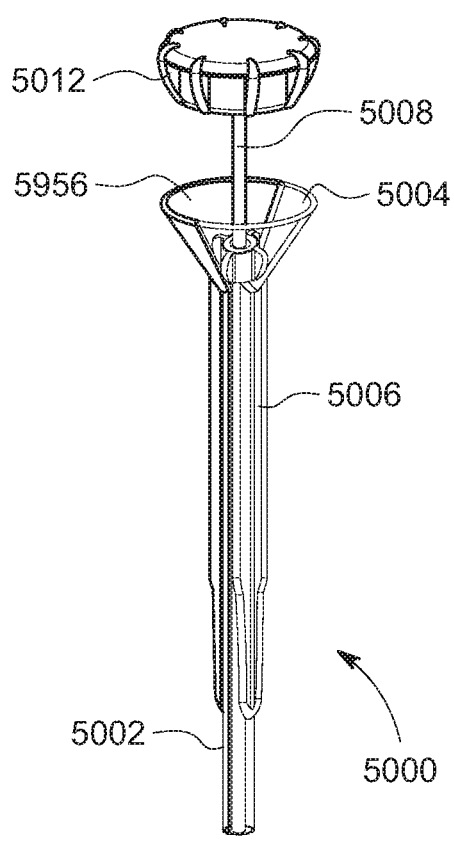
FIG. 27a is a perspective view of yet another apparatus for delivery of bone in accordance with yet another embodiment of the present invention.
Figure 27B:
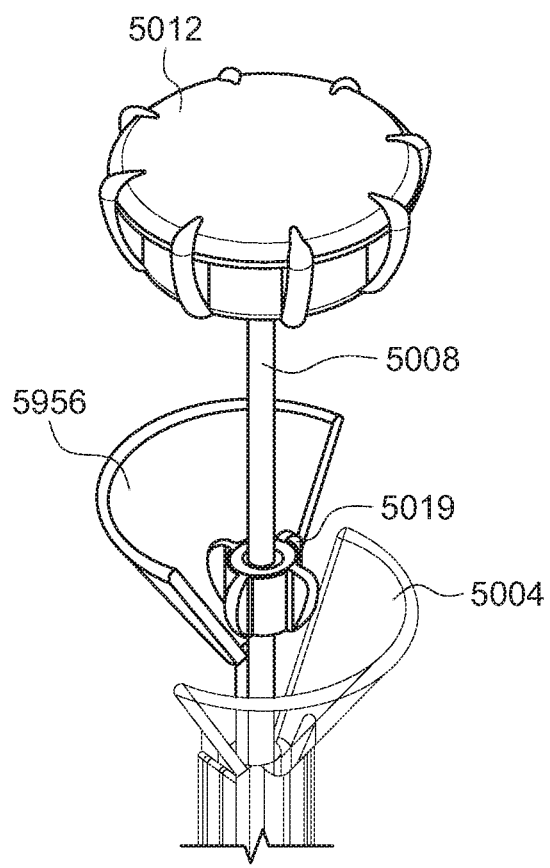
FIG. 27b is another perspective view of the apparatus of FIG. 27a focusing on an upper portion of the apparatus.
Figure 27C:
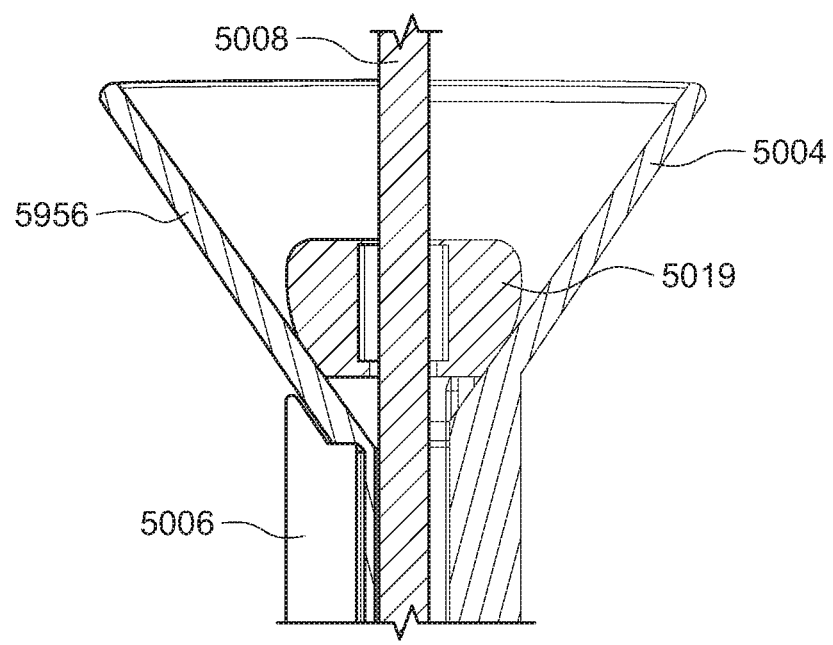

A perspective view of an apparatus for delivery of bone in accordance with a fourteenth embodiment of the present invention is shown in FIGS. 27a through 27c, and comprises a syringe 5000 comprising a tip 5002 at a bottom thereof, a top 2004, and a tubular section 5006 with a generally cylindrical interior wall defining a passageway extending from the top 5004 to the tip 5002. The syringe 5000 further comprises a plunger comprising an elongate piston 5008, a press head and a handle 5012, with the piston 5008 extending between the press head at a lower end of the plunger and the handle 5012 at an upper end of the plunger. The plunger is shown being fully received within the tubular section 5006 in FIGS. 27a and 27c.

In this illustrated embodiment, the tip 5002, the top 5004, and the tubular section 5006 preferably are formed by a single piece of molded material. Unlike for example, the top 1004, the top 5004 is not funnel-shaped but, instead, is only partially funnel-shaped. In this regard, the top 5956 of the cartridge 5952 preferably mates with the top 5004 when the shaft 5954 of the cartridge 5952 is fully received within the passageway of the tubular section 5006 so as to form a funnel at the top of the syringe 5000.

The plunger 1203 preferably comprises a single piece of molded material welding two individual pieces 2005a, 2005b of a molded material together. The seam between the pieces is perhaps best seen in the area of the funnel-shaped top at 2049 in FIG. 22a.

The plunger includes a collar 5019 through which the piston 5008 extends. The collar 5019 is positioned along the piston 5008 so as to limit advancement of the piston 5008 through the passageway beyond a predetermined extent. Preferably, the collar 5019 is held in frictional engagement with the piston 5008 and is adjustable up and down the piston 5008 by sliding upon application of sufficient force greater than that encountered when the collar 5019 engages the funnel-shaped top 5004 and acts as a stop. The piston 5008 preferably comprises a cylinder formed of a metal or metal alloy and is received within a bore of the handle 5012 in frictional fit therewith.

Use of the cartridges in the illustrated thirteenth and fourteenth embodiments is similar to the use described with the ninth embodiment. Furthermore, it will be appreciated that due to the partial-funnel shape of the top of the cartridge in the illustrated thirteenth and fourteenth embodiments, additional bone can be placed into the syringe and delivered without removing a used cartridge by using the funnel defined at the top of the syringe in these embodiments. Alternatively, the used cartridge preferably will fall out of the passageway of the tubular section when the syringe is inverted, making replacement of the cartridge by a technician or assistant to a surgeon a one-handed maneuver during an operation.

Apparatus for delivery of bone in accordance with further embodiments of the present invention still yet are disclosed in FIGS. 28-65 as briefly described above, and are disclosed in the incorporated Appendix.

Figures 28, 29:
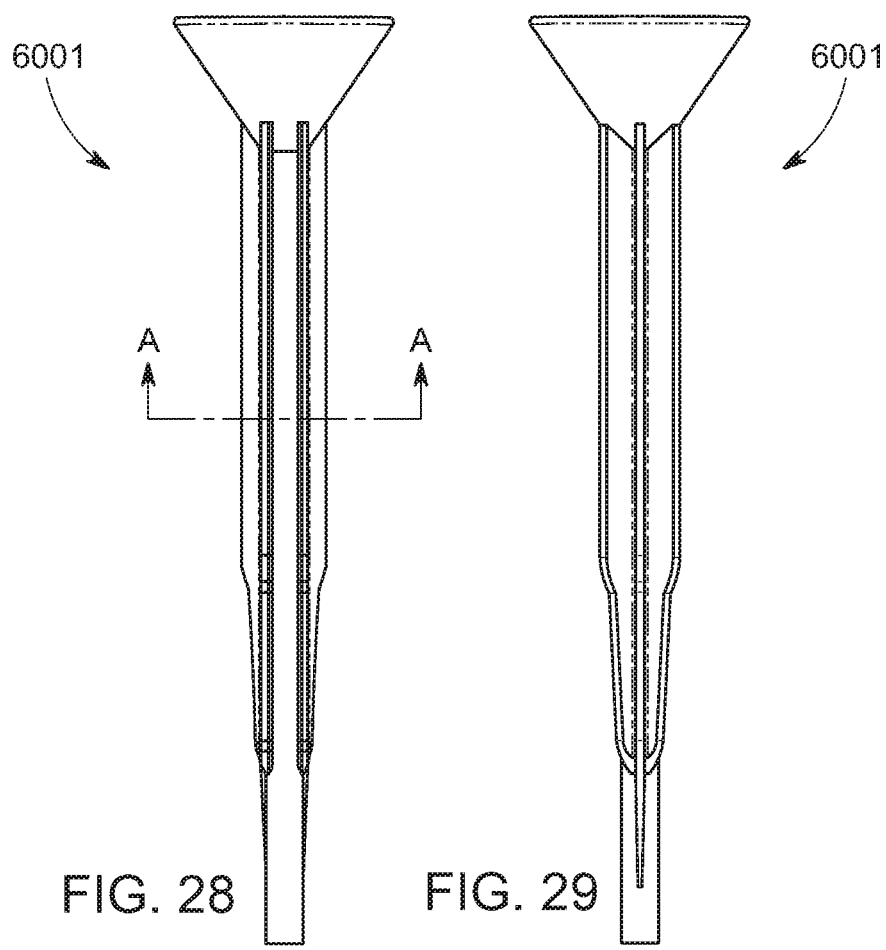
FIG. 28 is a side view of a body of a syringe used in an apparatus for delivery of bone in accordance with yet another embodiment of the present invention, wherein the syringe body is formed in a molding process and is a single integral molded piece.
FIG. 29 is an additional side view of the syringe body of FIG. 28.
Figures 30, 31:
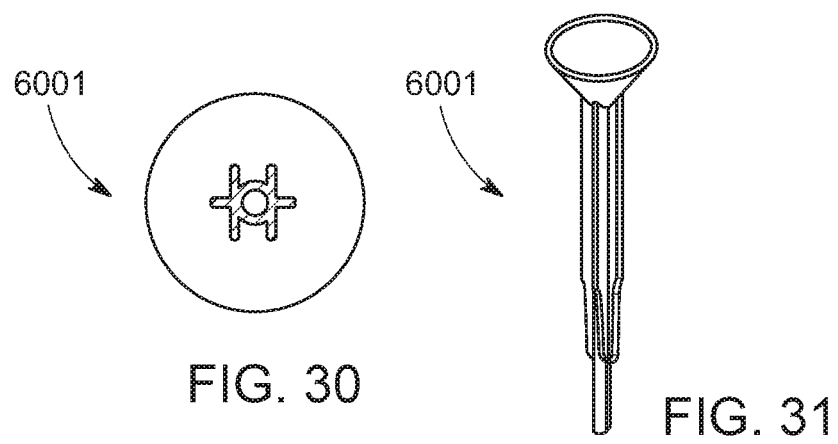
FIG. 30 is a cross-sectional view along the line A-A of FIG. 28.
FIG. 31 is a perspective view of the syringe body of FIG. 28.

Thus, FIG. 28 is a side view of a body 6001 of a syringe used in an apparatus for delivery of bone in accordance with yet another embodiment of the present invention, wherein the syringe body 6001 is formed in a molding process and is a single integral molded piece. FIG. 29 is an additional side view of the syringe body 6001; FIG. 30 is a cross-sectional view of the syringe body 6001 taken along the line A-A of FIG. 28; FIG. 31 is a perspective view of the syringe body 6001.

In contrast, FIG. 32 is a side view of a body 7001 of a syringe used in an apparatus for delivery of bone in accordance with yet another embodiment of the present invention, wherein the syringe body 7001 is formed by welding two body portions 7001a, 7001b together.

FIG. 33 is an additional side view of the syringe body of FIG. 32.

FIG. 34 is a cross-sectional view along the line B-B of FIG. 32.

FIG. 35 is a perspective view of the syringe body of FIG. 32.

FIG. 36 is an exploded perspective view of the syringe body of FIG. 32.

FIG. 37 is a perspective view of a plunger used in an apparatus for delivery of bone in accordance with yet another embodiment of the present invention.

FIG. 38 is a side view of the plunger of FIG. 37.

FIG. 39 is a cross-sectional view of the plunger of FIG. 38 taken along the line C-C.

FIG. 40 is a cross-sectional view of the plunger of FIG. 38 taken along the line D-D.

FIG. 41 is a view of the distal end of the plunger of FIG. 38.

FIG. 42 is a cross-sectional view of the distal end of FIG. 41 taken along the line N-N; it will be appreciated that as seen in FIGS. 41 and 42, the distal end of the plunger includes an overmolded wiper.

Figure 43:
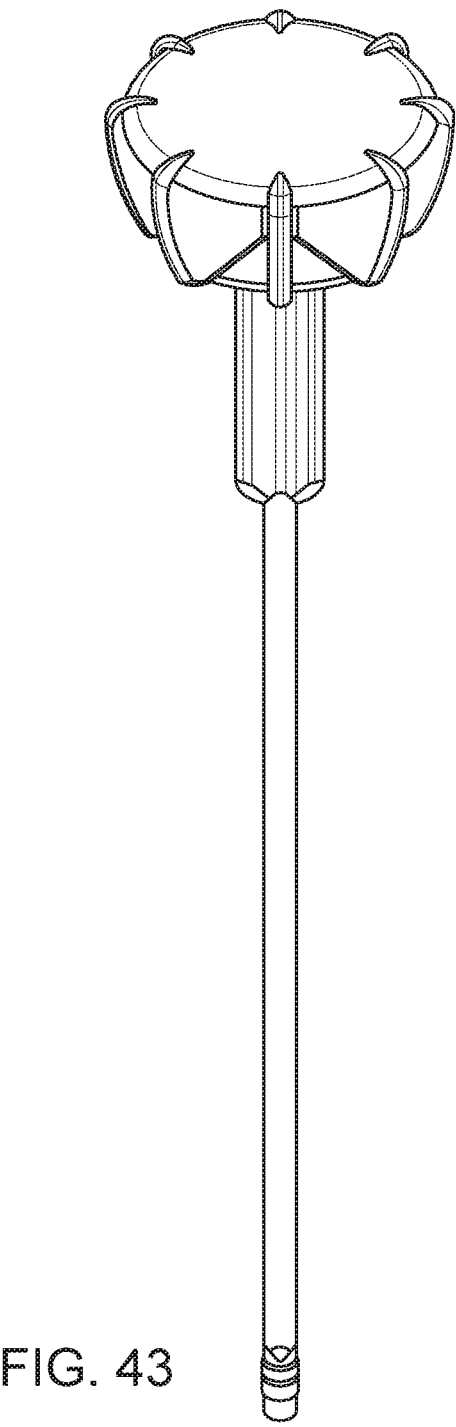
FIG. 43 is a shaded view of FIG. 37.

FIG. 43 is a shaded view of FIG. 37.

FIG. 44 is a perspective view of a plunger used in an apparatus for delivery of bone in accordance with yet another embodiment of the present invention.

FIG. 45 is a side view of the plunger of FIG. 44.

FIG. 46 is a cross-sectional view of the plunger of FIG. 45 taken along the line E-E.

FIG. 47 is a cross-sectional view of the plunger of FIG. 45 taken along the line F-F.

Figure 48:
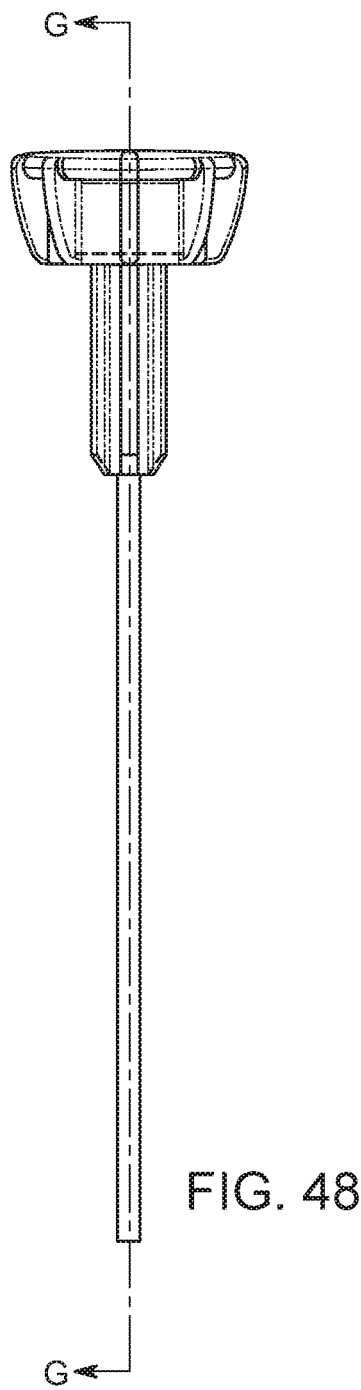
FIG. 48 is another side view of the plunger of FIG. 45.

FIG. 48 is another side view of the plunger of FIG. 45.

Figure 49:
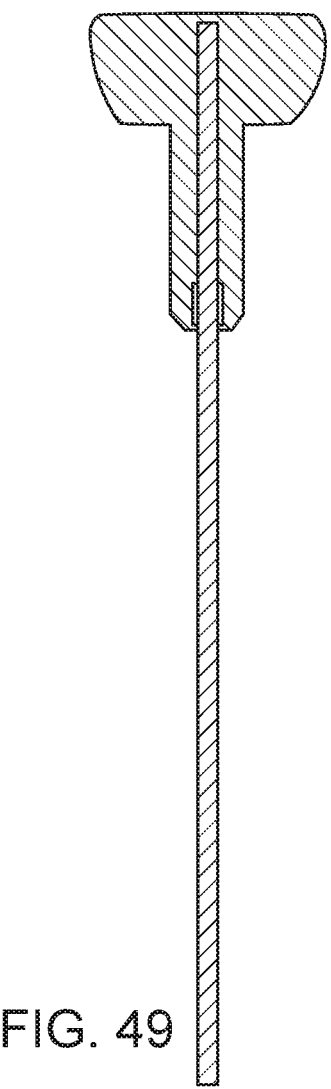
FIG. 49 is a cross-sectional view of the plunger of FIG. 48 taken along the line G-G; it will be appreciated that as seen in FIG. 49, the rod of the plunger is attached to the handle by pressing the rod into a bore of the handle whereby the rod is removably held in a friction-fit engagement.

FIG. 49 is a cross-sectional view of the plunger of FIG. 48 taken along the line G-G; it will be appreciated that as seen in FIG. 49, the rod of the plunger is attached to the handle by pressing the rod into a bore of the handle whereby the rod is removably held in a friction-fit engagement.

Figures 50, 51:
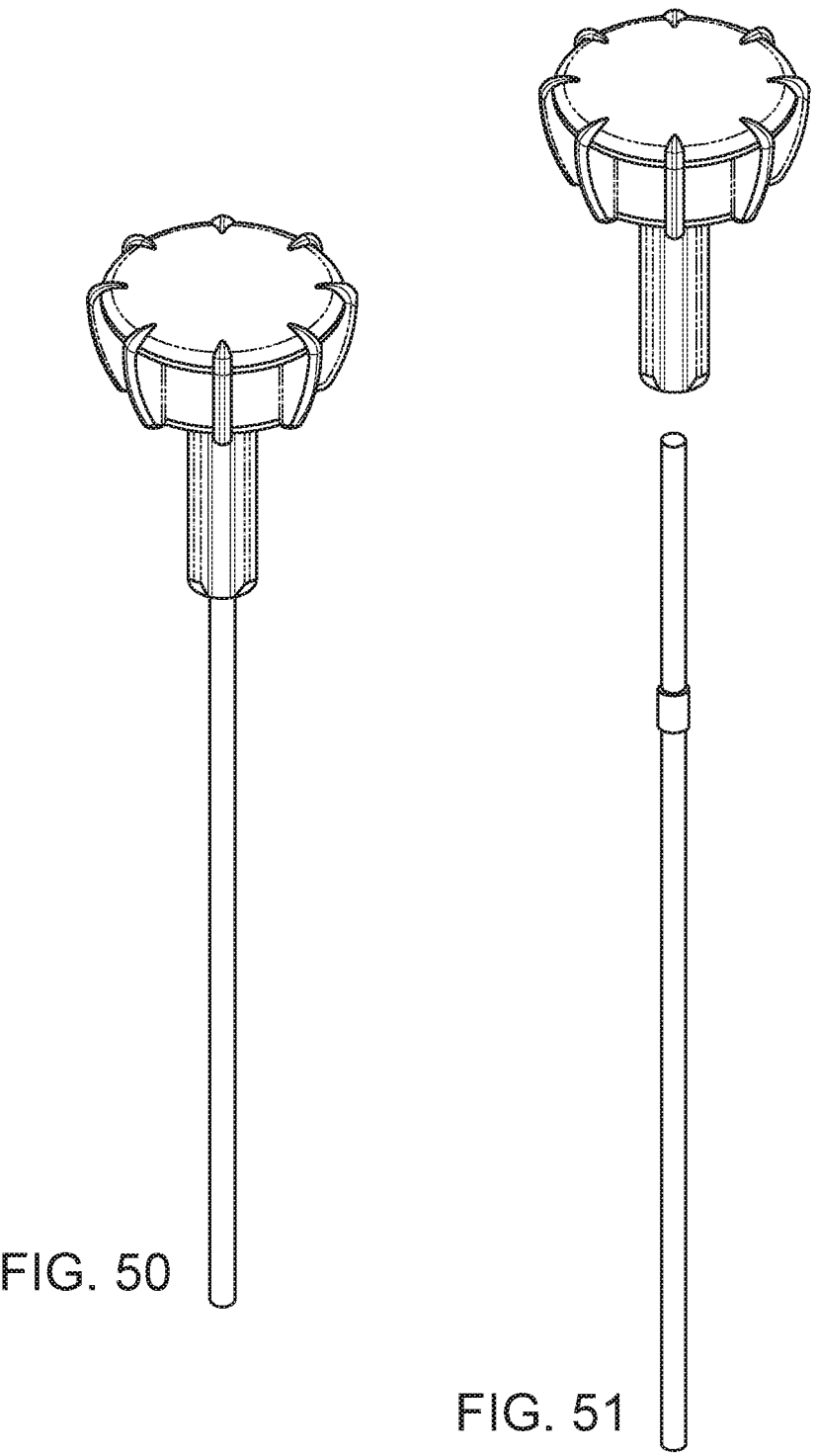
FIG. 50 is a shaded view of the plunger of FIG. 44.
FIG. 51 is an exploded view of the plunger of FIG. 50 illustrating separation of the handle from the rod.

FIG. 50 is a shaded view of the plunger of FIG. 44.

FIG. 51 is an exploded view of the plunger of FIG. 50 illustrating separation of the handle from the rod.

FIG. 52 is a perspective view of a plunger used in an apparatus for delivery of bone in accordance with yet another embodiment of the present invention.

FIG. 53 is a side view of the plunger of FIG. 52.

FIG. 54 is a cross-sectional view of the plunger of FIG. 53 taken along the line H-H.

FIG. 55 is a cross-sectional view of the plunger of FIG. 53 taken along the line L-L.

Figures 56, 57:
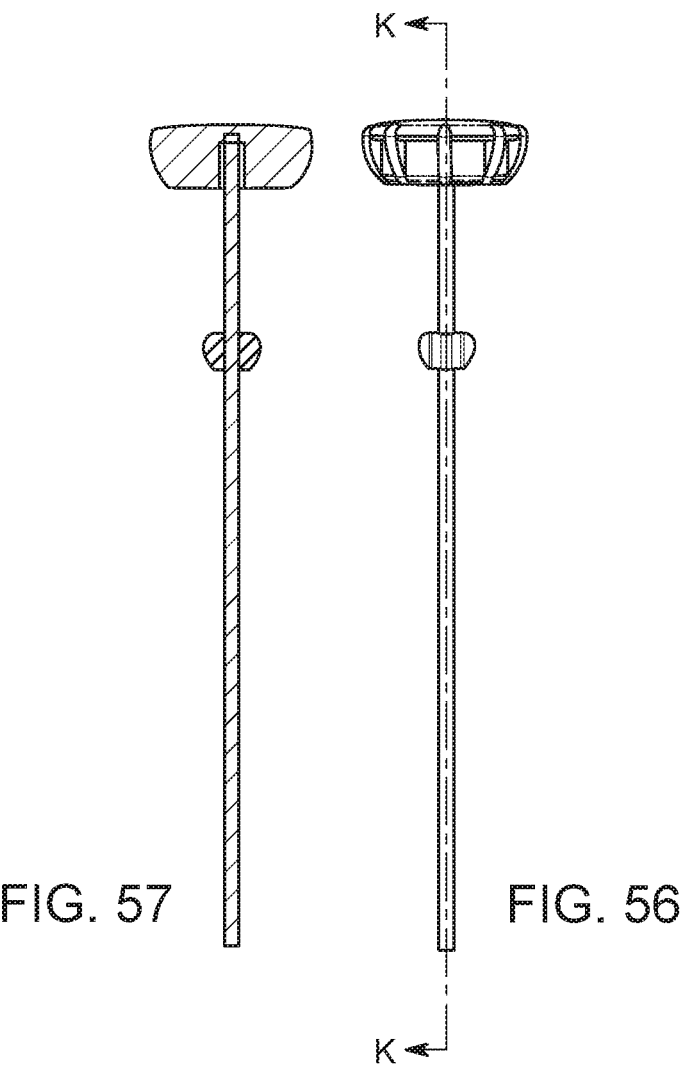
FIG. 56 is another side view of the plunger of FIG. 53.
FIG. 57 is a cross-sectional view of the plunger of FIG. 56 taken along the line K-K; it will be appreciated that as seen in FIG. 57, the rod of the plunger is attached to the handle by pressing the rod into a bore of the handle whereby the rod is removably held in a friction-fit engagement, and similarly, the collar of the plunger is attached to the rod by pressing the collar onto the piston of the plunger whereby the collar is held in a friction-fit engagement to the piston.

FIG. 56 is another side view of the plunger of FIG. 53.

FIG. 57 is a cross-sectional view of the plunger of FIG. 56 taken along the line K-K; it will be appreciated that as seen in FIG. 57, the rod of the plunger is attached to the handle by pressing the rod into a bore of the handle whereby the rod is removably held in a friction-fit engagement, and similarly, the collar of the plunger is attached to the rod by pressing the collar onto the piston of the plunger whereby the collar is held in a friction-fit engagement to the piston.

Figures 58, 59:
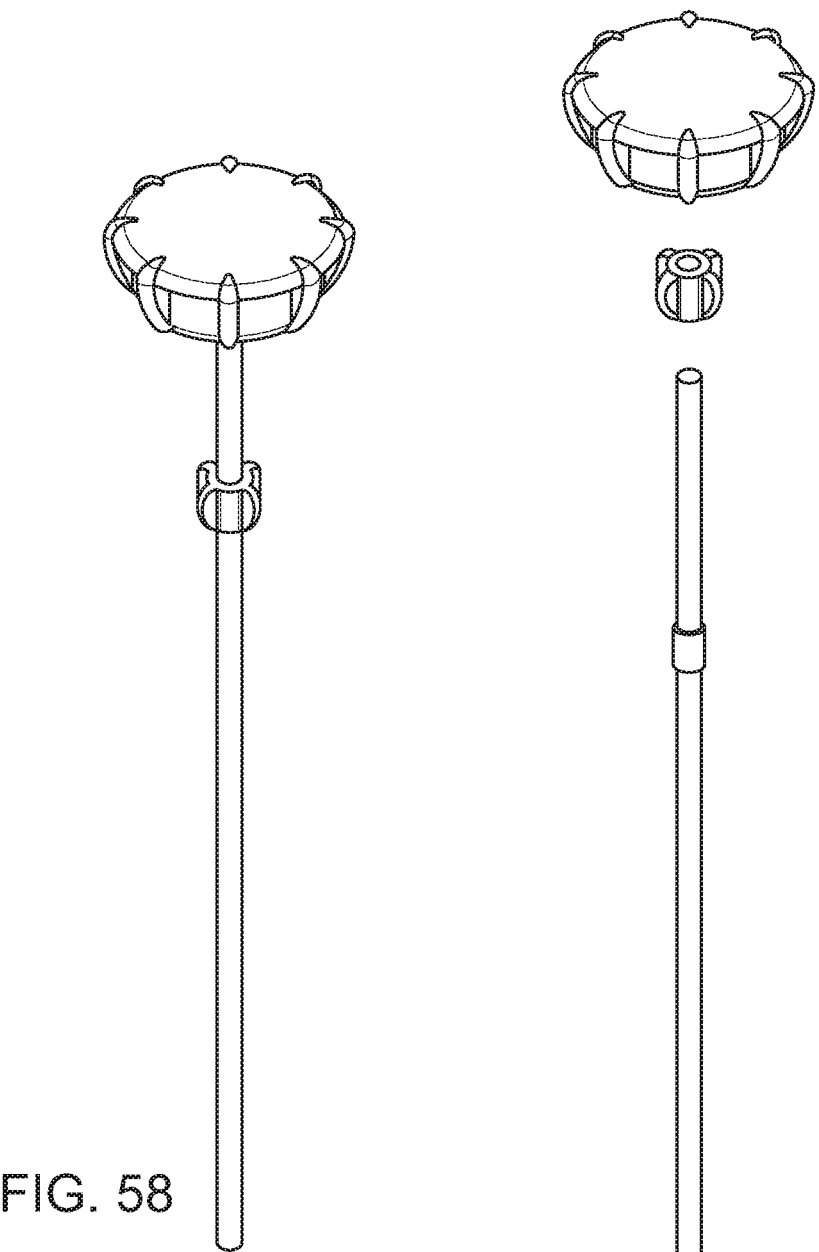
FIG. 58 is a shaded view of the plunger of FIG. 52.
FIG. 59 is an exploded view of the plunger of FIG. 58 illustrating separation of the handle from the rod and the collar from the rod.

FIG. 58 is a shaded view of the plunger of FIG. 52.

FIG. 59 is an exploded view of the plunger of FIG. 58 illustrating separation of the handle from the rod and the collar from the rod.

Figure 60:
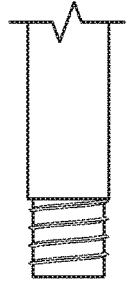
FIG. 60 illustrates a side view of a distal end portion of a syringe body for use in an apparatus for delivery of bone in accordance with yet another embodiment of the present invention, wherein the distal end includes threads by which a tip is removably attachable in threaded engagement by screwing the tip thereon.

FIG. 60 illustrates a side view of a distal end portion of a syringe body for use in an apparatus for delivery of bone in accordance with yet another embodiment of the present invention, wherein the distal end includes threads by which a tip is removably attachable in threaded engagement by screwing the tip thereon.

Figure 61:
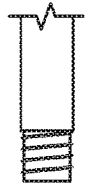
FIG. 61 illustrates the screwing of a tip onto the distal end portion shown in FIG. 60.

FIG. 61 illustrates the screwing of a tip onto the distal end portion shown in FIG. 60.

Figure 62:
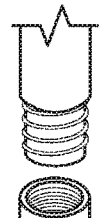
FIG. 62 also illustrates, in perspective view, the screwing of the tip onto the distal end portion as seen in FIG. 61.

FIG. 62 also illustrates, in perspective view, the screwing of the tip onto the distal end portion as seen in FIG. 61.

Figure 63:
FIG. 63 illustrates in perspective view the tip of FIG. 62, wherein a small diameter for delivery of bone is seen.

FIG. 63 illustrates in perspective view the tip of FIG. 62, wherein a small diameter for delivery of bone is seen.

Figure 64:
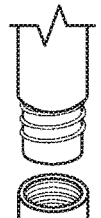
FIG. 64, which is similar to FIG. 62, illustrates in perspective view the screwing of a tip onto the distal end portion of FIG. 60, which tip is different from but interchangeable with the tip of FIG. 62.

FIG. 64, which is similar to FIG. 62, illustrates in perspective view the screwing of a tip onto the distal end portion of FIG. 60, which tip is different from but interchangeable with the tip of FIG. 62.

Figure 65:
FIG. 65 illustrates in perspective view the tip of FIG. 64 and reveals a diameter for delivery of bone that is larger than the diameter of the tip of FIG. 63.

FIG. 65 illustrates in perspective view the tip of FIG. 64 and reveals a diameter for delivery of bone that is larger than the diameter of the tip of FIG. 63.

Based on the foregoing description, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention.

Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements, the present invention being limited only by the claims appended hereto and the equivalents thereof.

What is claimed is:

1. A method for loading an apparatus for delivery of bone to a patient during a surgical operation, the apparatus comprising a body including a funnel-shaped top, a lower tip, and a tubular section with a generally cylindrical interior wall defining a passageway extending therebetween, the method comprising inserting a single cartridge into the passageway, wherein the cartridge comprises a tube having open ends and having a curved cross-section generally matching that of the generally cylindrical interior wall of the passageway of the tubular section, wherein a longitudinal opening extends the length of the tube thereby facilitating radial placement and packing of bone within the tube along the extent of the tube, and wherein the tube is prefilled with an amount of bone such that the bone does not extend beyond the juncture of the tubular section and the funnel-shaped top when the tube is fully received within the passageway; and further comprising a preliminary step of preparing the cartridge for insertion by radially placing and packing bone within the tube along the extent of the tube by positioning bone through the longitudinal opening without passing bone through the open ends of the tube.

2. The method of claim 1, wherein the outer diameter of the tube generally corresponds to the inner diameter of the generally cylindrical interior wall of the passageway, with the tube being slightly smaller such that the tube is be received in close fit with the generally cylindrical interior wall of the passageway, the single tube thereby lining the generally cylindrical interior wall of the passageway.

3. The method of claim 1, wherein the tube is made of a metal or metal alloy.

4. The method of claim 1, wherein a length of the tube at least equals the length of the tubular section such that the tube is received within the entire length of the passageway defined by the tubular section.

5. The method of claim 1, wherein a length of the tube exceeds the length of the tubular section such that the tube is received within the entire length of the passageway defined by the tubular section.

6. The method of claim 1, wherein the tube presents an end extent for gripping by hand for insertion into and removal from the passageway.

7. The method of claim 1, further comprising using a plunger having an outer diameter generally corresponding to the inner diameter of the tube to push bone from the tube out of the tip of the apparatus.

8. The method of claim 1, further comprising interchanging an emptied tube with another prefilled tube during the surgical procedure.

\* \* \* \* \*